US012414998B2

(12) United States Patent
Kim et al.

(10) Patent No.: US 12,414,998 B2
(45) Date of Patent: Sep. 16, 2025

(54) ANTI-HER2 AFFIBODY AND SWITCHABLE CHIMERIC ANTIGEN RECEPTOR USING SAME AS SWITCH MOLECULE

(71) Applicant: ABCLON INC., Seoul (KR)

(72) Inventors: Ki Hyun Kim, Seoul (KR); Hyun-Jong Lee, Incheon (KR); Jong-Seo Lee, Gyeonggi-do (KR)

(73) Assignee: ABCLON INC., Seoul (KR)

( * ) Notice: Subject to any disclaimer, the term of this patent is extended or adjusted under 35 U.S.C. 154(b) by 0 days.

(21) Appl. No.: 17/424,970

(22) PCT Filed: Apr. 16, 2021

(86) PCT No.: PCT/KR2021/004793

§ 371 (c)(1),
(2) Date: Jul. 22, 2021

(87) PCT Pub. No.: WO2021/210939

PCT Pub. Date: Oct. 21, 2021

(65) Prior Publication Data

US 2022/0315666 A1 Oct. 6, 2022

(30) Foreign Application Priority Data

Apr. 17, 2020 (KR) ........................ 10-2020-0047025

(51) Int. Cl.

| | |
|---|---|
| ***C07K 16/32*** | (2006.01) |
| ***A61K 40/11*** | (2025.01) |
| ***A61K 40/31*** | (2025.01) |
| ***A61K 40/33*** | (2025.01) |
| ***A61K 40/42*** | (2025.01) |
| ***A61K 47/54*** | (2017.01) |
| ***A61K 47/68*** | (2017.01) |
| ***C12N 5/0783*** | (2010.01) |
| *A61K 39/00* | (2006.01) |

(52) U.S. Cl.

CPC .......... *A61K 47/6855* (2017.08); *A61K 40/11* (2025.01); *A61K 40/31* (2025.01); *A61K 40/33* (2025.01); *A61K 40/4205* (2025.01); *A61K 47/545* (2017.08); *A61K 47/6803* (2017.08); *A61K 47/6851* (2017.08); *C07K 16/32* (2013.01); *C12N 5/0636* (2013.01); *A61K 2039/505* (2013.01); *A61K 2239/23* (2023.05); *A61K 2239/31* (2023.05); *A61K 2239/38* (2023.05); *A61K 2239/59* (2023.05); *C07K 2317/73* (2013.01); *C07K 2317/92* (2013.01); *C07K 2319/02* (2013.01); *C07K 2319/03* (2013.01); *C07K 2319/33* (2013.01)

(58) Field of Classification Search

None

See application file for complete search history.

(56) References Cited

U.S. PATENT DOCUMENTS

| | | | | |
|---|---|---|---|---|
| 11,167,037 | B2 * | 11/2021 | Chung ................. | C07K 16/468 |
| 2011/0160430 | A1 | 6/2011 | de Jesus et al. | |
| 2014/0088021 | A1 | 3/2014 | Riggs-Sauthier et al. | |
| 2015/0307564 | A1 | 10/2015 | Young et al. | |
| 2016/0144062 | A1 | 5/2016 | Hiscock et al. | |

FOREIGN PATENT DOCUMENTS

| | | | |
|---|---|---|---|
| CN | 1816563 | A | 8/2006 |
| KR | 1020180031727 | A | 9/2020 |
| KR | 1020190121716 | A | 5/2021 |
| WO | WO-1995/019374 | A1 | 7/1995 |
| WO | WO-2009/080811 | A1 | 7/2009 |
| WO | WO-2012/096760 | A1 | 7/2012 |
| WO | WO-2018128485 | A | 7/2018 |
| WO | WO-2019/203600 | A1 | 10/2019 |

OTHER PUBLICATIONS

Notice of Allowance from correspinding Korean Patent Application No. 10-2020-0047025, dated Dec. 23, 2022.

Full wwPDB NMR Structure Validation Report, Worldwide PDB Protein Data Bank, May 28, 2020, pp. 1-14.

Eigenbrot, C., et al.; "Structural basis for high-affinity HER2 receptor binding by an engineered protein", PNAS, Aug. 24, 2010, vol. 107, No. 34, 15039-15044.

Office Action from corresponding Chinese Patent Application No. 202180001956.1, dated May 11, 2023.

International Search Report from PCT Application No. PCT/KR2021/004793.

Office Action from corresponding Japanese Patent Application No. 2021-549988, dated Aug. 10, 2022.

Orlova Anna et al:"Tumor imaging using a picomolar affinity HER2 binding affibody molecule", Cancer Research, American Association for Cancer Research, US,vol. 66, No. 8, Apr. 15, 2006 (Apr. 15, 2006), pp. 4339-4348, XP002488605.

Zhen Cheng et al: "64Cu-Labeled Affibody Molecules for Imaging of HER2 Expressing Tumors", Molecular Imaging and Biology, Springer-Verlag, NE, vol. 12, No. 3, Sep. 25, 2009 (Sep. 25, 2009), pp. 316-324, XP019833345.

Extended European Search Report from corresponding European Patent Application No. 21743362.2, dated Apr. 12, 2024.

* cited by examiner

*Primary Examiner* — Daniel E Kolker
*Assistant Examiner* — James Ryland Melchior
(74) *Attorney, Agent, or Firm* — Harness, Dickey & Pierce, P.L.C.

(57) ABSTRACT

Disclosed herein are an anti-HER2 affibody and a switch molecule including a cotinine-conjugated anti-HER2 affibody. When applied in combination with Cot-sCART, the cotinine-conjugated anti-HER2 affibody reacts with HER2-positive cells to induce immune cell activity, thereby finding advantageous applications as switch molecules in sCART therapeutic agents.

10 Claims, 20 Drawing Sheets

Specification includes a Sequence Listing.

SEQUENCE LISTING

```
<160> NUMBER OF SEQ ID NOS: 31

<210> SEQ ID NO 1
<211> LENGTH: 58
<212> TYPE: PRT
<213> ORGANISM: Artificial Sequence
<220> FEATURE:
<223> OTHER INFORMATION: ZQAA1

<400> SEQUENCE: 1

Val Asp Asn Lys Phe Asn Lys Glu Leu Arg Val Ala Tyr Trp Glu Ile
1               5                   10                  15

Val Lys Leu Pro Asn Leu Asn Pro Tyr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 2
<211> LENGTH: 58
<212> TYPE: PRT
<213> ORGANISM: Artificial Sequence
<220> FEATURE:
<223> OTHER INFORMATION: ZQAA7

<400> SEQUENCE: 2

Val Asp Asn Lys Phe Asn Lys Glu Leu Arg Gly Ala Tyr Trp Glu Ile
1               5                   10                  15

Thr Ser Leu Pro Asn Leu Asn His Ser Gln Ile Thr Ala Phe Ile Val
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 3
<211> LENGTH: 58
<212> TYPE: PRT
<213> ORGANISM: Artificial Sequence
<220> FEATURE:
<223> OTHER INFORMATION: ZQAA8

<400> SEQUENCE: 3

Val Asp Asn Lys Phe Asn Lys Glu Met Arg Asp Ala Tyr Trp Glu Ile
1               5                   10                  15

Val Arg Leu Pro Asn Leu Asn Pro Pro Gln Ser Thr Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 4
<211> LENGTH: 58
<212> TYPE: PRT
<213> ORGANISM: Artificial Sequence
<220> FEATURE:
<223> OTHER INFORMATION: ZQAA11

<400> SEQUENCE: 4

Val Asp Asn Lys Phe Asn Lys Glu Tyr Met Leu Ala Tyr Trp Glu Ile
```

```
1               5                   10                  15

Val Lys Leu Pro Asn Leu Asn Tyr Pro Gln Gln His Ala Phe Ile Arg
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 5
<211> LENGTH: 58
<212> TYPE: PRT
<213> ORGANISM: Artificial Sequence
<220> FEATURE:
<223> OTHER INFORMATION: ZQAA22

<400> SEQUENCE: 5

Val Asp Asn Lys Phe Asn Lys Glu Ile Asn Lys Ala Tyr Trp Glu Ile
1               5                   10                  15

Ile Ser Leu Pro Asn Leu Asn Lys Glu Gln His His Ala Phe Ile His
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 6
<211> LENGTH: 58
<212> TYPE: PRT
<213> ORGANISM: Artificial Sequence
<220> FEATURE:
<223> OTHER INFORMATION: ZQAA1234

<400> SEQUENCE: 6

Val Asp Asn Lys Phe Asn Lys Glu Leu Arg Val Ala Tyr Trp Glu Ile
1               5                   10                  15

Val Lys Leu Pro Asn Leu Asn Pro Pro Gln Ile Thr Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 7
<211> LENGTH: 58
<212> TYPE: PRT
<213> ORGANISM: Artificial Sequence
<220> FEATURE:
<223> OTHER INFORMATION: ZQAA1239

<400> SEQUENCE: 7

Val Asp Asn Lys Phe Asn Lys Glu Leu Arg Val Ala Tyr Trp Glu Ile
1               5                   10                  15

Val Lys Leu Pro Asn Leu Asn Pro Lys Gln Ile Thr Ala Phe Ile Lys
            20                  25                  30

Gln Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 8
```

<211> LENGTH: 58
<212> TYPE: PRT
<213> ORGANISM: Artificial Sequence
<220> FEATURE:
<223> OTHER INFORMATION: ZQAA8293

<400> SEQUENCE: 8

Val Asp Asn Lys Phe Asn Lys Glu Met Arg Asp Ala Tyr Trp Glu Ile
1 5 10 15

Val Arg Leu Pro Asn Leu Asn Arg Ile Gln Ser Val Ala Phe Ile Arg
20 25 30

Gln Leu Tyr Asp Asp Pro Ser Gln Ser Ala Asn Leu Leu Ala Glu Ala
35 40 45

Lys Lys Leu Asn Asp Ala Gln Ala Pro Lys
50 55

<210> SEQ ID NO 9
<211> LENGTH: 5
<212> TYPE: PRT
<213> ORGANISM: Artificial Sequence
<220> FEATURE:
<223> OTHER INFORMATION: CDRH1 of Anti-cotinine antibody

<400> SEQUENCE: 9

Arg Asp Trp Met Asn
1 5

<210> SEQ ID NO 10
<211> LENGTH: 15
<212> TYPE: PRT
<213> ORGANISM: Artificial Sequence
<220> FEATURE:
<223> OTHER INFORMATION: CDRH2 of Anti-cotinine antibody

<400> SEQUENCE: 10

Ala Ile Gly Arg Ser Gly Asp Thr Tyr Tyr Ala Thr Trp Ala Lys
1 5 10 15

<210> SEQ ID NO 11
<211> LENGTH: 11
<212> TYPE: PRT
<213> ORGANISM: Artificial Sequence
<220> FEATURE:
<223> OTHER INFORMATION: CDRH3 of Anti-cotinine antibody

<400> SEQUENCE: 11

Ile Pro Tyr Phe Gly Trp Asn Asn Gly Asp Ile
1 5 10

<210> SEQ ID NO 12
<211> LENGTH: 13
<212> TYPE: PRT
<213> ORGANISM: Artificial Sequence
<220> FEATURE:
<223> OTHER INFORMATION: CDRL1 of Anti-cotinine antibody

<400> SEQUENCE: 12

Gln Ser Ser Gln Ser Pro Tyr Ser Asn Glu Trp Leu Ser
1 5 10

<210> SEQ ID NO 13
<211> LENGTH: 7
<212> TYPE: PRT
<213> ORGANISM: Artificial Sequence
<220> FEATURE:
<223> OTHER INFORMATION: CDRL2 of Anti-cotinine antibody

<400> SEQUENCE: 13

Arg Ile Ser Thr Leu Ala Ser
1 5

<210> SEQ ID NO 14
<211> LENGTH: 12
<212> TYPE: PRT
<213> ORGANISM: Artificial Sequence
<220> FEATURE:
<223> OTHER INFORMATION: CDRL3 of Anti-cotinine antibody

<400> SEQUENCE: 14

Ala Gly Gly Tyr Asn Phe Gly Leu Phe Leu Phe Gly
1 5 10

<210> SEQ ID NO 15
<211> LENGTH: 119
<212> TYPE: PRT
<213> ORGANISM: Artificial Sequence
<220> FEATURE:
<223> OTHER INFORMATION: Heavy chain of Anti-cotinine antibody

<400> SEQUENCE: 15

Glu Val Gln Leu Val Glu Ser Gly Gly Gly Leu Val Gln Pro Gly Gly
1 5 10 15

Ser Leu Arg Leu Ser Cys Ala Ala Ser Gly His Leu Arg Arg Arg Asp
20 25 30

Trp Met Asn Trp Val Arg Gln Ala Pro Gly Lys Gly Leu Glu Trp Val
35 40 45

Ala Ala Ile Gly Arg Ser Gly Asp Thr Tyr Tyr Ala Thr Trp Ala Lys
50 55 60

Gly Arg Phe Thr Ile Ser Ala Asp Thr Ser Lys Asn Thr Ala Tyr Leu
65 70 75 80

Gln Met Asn Ser Leu Arg Ala Glu Asp Thr Ala Val Tyr Tyr Cys Ser
85 90 95

Arg Ile Pro Tyr Phe Gly Trp Asn Asn Gly Asp Ile Trp Gly Gln Gly
100 105 110

Thr Leu Val Thr Val Ser Ser
115

<210> SEQ ID NO 16
<211> LENGTH: 357
<212> TYPE: DNA
<213> ORGANISM: Artificial Sequence
<220> FEATURE:
<223> OTHER INFORMATION: Heavy chain of Anti-cotinine antibody

<400> SEQUENCE: 16
gaggtgcagc tggtggagtc tggcggcgga ctggtgcagc ctggcggaag cttgcggctg 60
tcctgcgccg cctccgggca tcttcggagg agggactgga tgaactgggt gcggcaggcc 120
cctggcaagg gcctagagtg ggtggccgcc attggtagaa gtggagacac atactacgcg 180
acctgggcga aaggccggtt caccatctcc gccgacacct ccaagaacac cgcctacctg 240
cagatgaact ccctgcgggc cgaggacacc gccgtgtact actgctccag aattccttat 300
tttggttgga ataatggtga catctggggc cagggcacac tcgtgaccgt gtcctcc 357

<210> SEQ ID NO 17
<211> LENGTH: 110
<212> TYPE: PRT

<213> ORGANISM: Artificial Sequence
<220> FEATURE:
<223> OTHER INFORMATION: Light chain of Anti-cotinine antibody

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Pro Tyr Ser Asn
            20                  25                  30

Glu Trp Leu Ser Trp Tyr Gln Gln Lys Pro Gly Lys Ala Pro Lys Leu
        35                  40                  45

Leu Ile Tyr Arg Ile Ser Thr Leu Ala Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Asn Phe
                85                  90                  95

Gly Leu Phe Leu Phe Gly Gln Gly Thr Lys Val Glu Ile Lys
            100                 105                 110
```

<210> SEQ ID NO 18
<211> LENGTH: 330
<212> TYPE: DNA
<213> ORGANISM: Artificial Sequence
<220> FEATURE:
<223> OTHER INFORMATION: Light chain of Anti-cotinine antibody

<400> SEQUENCE: 18

```
gacatccaga tgacccagtc cccctcctcg ctgagcgcct ccgtgggcga ccgggtgacc     60

atcacctgcc agtccagtca gagtccttat agtaacgagt ggttatcctg gtatcagcag    120

aagcctggca aggcgcctaa gctgctgatc tacaggatat ccactctggc atctggcgtg    180

ccttcccggt tctccggatc ccggtccggc accgacttca ccctgaccat ctcctccctg    240

caacctgagg acttcgccac ctactactgc gcaggcggtt ataattttgg tttgtttctc    300

ttcggccagg gtaccaaggt ggagatcaag                                     330
```

<210> SEQ ID NO 19
<211> LENGTH: 1184
<212> TYPE: DNA
<213> ORGANISM: Artificial Sequence
<220> FEATURE:
<223> OTHER INFORMATION: EF-1alpha promoter

<400> SEQUENCE: 19

```
tgtgaggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600
```

-continued

```
gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttggggggag gggttttatg   1020

cgatggagtt tccccacact gagtgggtgg agactgaagt taggccagct tggcacttga   1080

tgtaattctc cttggaattt gccctttttg agtttggatc ttggttcatt ctcaagcctc   1140

agacagtggt tcaaagtttt tttcttccat ttcaggtgtc gtga                    1184


<210> SEQ ID NO 20
<211> LENGTH: 63
<212> TYPE: DNA
<213> ORGANISM: Artificial Sequence
<220> FEATURE:
<223> OTHER INFORMATION: CD8 leader

<400> SEQUENCE: 20

atggccctgc ctgtgaccgc tctgctgctg cccctggctc tgctgctgca cgccgctcgc     60

ccc                                                                   63


<210> SEQ ID NO 21
<211> LENGTH: 207
<212> TYPE: DNA
<213> ORGANISM: Artificial Sequence
<220> FEATURE:
<223> OTHER INFORMATION: CD8 hinge and TM region

<400> SEQUENCE: 21

accacaactc cagctccccg gccccctacc cctgcaccaa caatcgccag ccagcctctg     60

tccctgagac cagaggcatg taggccagct gcaggaggag cagtgcatac aagaggcctg    120

gacttcgcct gcgatatcta catttgggct cctctggcag gaacttgtgg cgtgctgctg    180

ctgtctctgg tcatcaccct gtactgc                                        207


<210> SEQ ID NO 22
<211> LENGTH: 126
<212> TYPE: DNA
<213> ORGANISM: Artificial Sequence
<220> FEATURE:
<223> OTHER INFORMATION: CD137

<400> SEQUENCE: 22

aaaaggggcc gcaagaaact gctgtatatt ttcaagcagc ccttcatgcg gcccgtgcag     60

accacacagg aggaagacgg gtgctcctgt agattccccg aggaagagga aggcgggtgt    120

gagctg                                                               126


<210> SEQ ID NO 23
<211> LENGTH: 336
<212> TYPE: DNA
<213> ORGANISM: Artificial Sequence
<220> FEATURE:
<223> OTHER INFORMATION: CD3z

<400> SEQUENCE: 23

cgcgtcaagt tcagccgatc agccgatgct cctgcataca agcagggcca gaatcagctg     60
```

```
tataacgagc tgaatctggg gcgccgagag gaatacgacg tgctggataa gcggagaggg    120

agggaccccg aaatgggagg caaacctagg cgcaagaacc cacaggaggg actgtacaat    180

gaactgcaga aggacaaaat ggccgaggct tattccgaaa ttgggatgaa aggagagcga    240

cggagaggga agggacacga tgggctgtat cagggactgt ctaccgccac taaagatacc    300

tacgacgctc tgcacatgca ggctctgcca cctcgc                              336
```

```
<210> SEQ ID NO 24
<211> LENGTH: 58
<212> TYPE: PRT
<213> ORGANISM: Artificial Sequence
<220> FEATURE:
<223> OTHER INFORMATION: General Formula for anti-HER2 affibody
<220> FEATURE:
<221> NAME/KEY: VARIANT
<222> LOCATION: (9)..(11)
<223> OTHER INFORMATION: X can be independently any amino acid
<220> FEATURE:
<221> NAME/KEY: VARIANT
<222> LOCATION: (17)..(18)
<223> OTHER INFORMATION: X can be independently any amino acid
<220> FEATURE:
<221> NAME/KEY: VARIANT
<222> LOCATION: (24)..(25)
<223> OTHER INFORMATION: X can be independently any amino acid
<220> FEATURE:
<221> NAME/KEY: VARIANT
<222> LOCATION: (27)..(28)
<223> OTHER INFORMATION: X can be independently any amino acid
<220> FEATURE:
<221> NAME/KEY: VARIANT
<222> LOCATION: (32)..(33)
<223> OTHER INFORMATION: X can be independently any amino acid
<220> FEATURE:
<221> NAME/KEY: VARIANT
<222> LOCATION: (35)..(35)
<223> OTHER INFORMATION: X can be independently any amino acid

<400> SEQUENCE: 24

Val Asp Asn Lys Phe Asn Lys Glu Xaa Xaa Xaa Ala Tyr Trp Glu Ile
1               5                   10                  15

Xaa Xaa Leu Pro Asn Leu Asn Xaa Xaa Gln Xaa Xaa Ala Phe Ile Xaa
            20                  25                  30

Xaa Leu Xaa Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 25
<211> LENGTH: 15
<212> TYPE: PRT
<213> ORGANISM: Artificial Sequence
<220> FEATURE:
<223> OTHER INFORMATION: Linker

<400> SEQUENCE: 25

Gly Gly Gly Gly Ser Gly Gly Gly Gly Ser Gly Gly Gly Gly Ser
1               5                   10                  15


<210> SEQ ID NO 26
<211> LENGTH: 15
<212> TYPE: PRT
<213> ORGANISM: Artificial Sequence
<220> FEATURE:
<223> OTHER INFORMATION: Linker

<400> SEQUENCE: 26
```

```
Ser Ser Ser Ser Gly Ser Ser Ser Ser Gly Ser Ser Ser Ser Gly
1               5                   10                  15


<210> SEQ ID NO 27
<211> LENGTH: 5
<212> TYPE: PRT
<213> ORGANISM: Artificial Sequence
<220> FEATURE:
<223> OTHER INFORMATION: Linker

<400> SEQUENCE: 27

Gly Gly Gly Gly Ser
1               5


<210> SEQ ID NO 28
<211> LENGTH: 4
<212> TYPE: PRT
<213> ORGANISM: Artificial Sequence
<220> FEATURE:
<223> OTHER INFORMATION: Linker

<400> SEQUENCE: 28

Val Asp Gly Ser
1


<210> SEQ ID NO 29
<211> LENGTH: 4
<212> TYPE: PRT
<213> ORGANISM: Artificial Sequence
<220> FEATURE:
<223> OTHER INFORMATION: Linker

<400> SEQUENCE: 29

Ala Ser Gly Ser
1


<210> SEQ ID NO 30
<211> LENGTH: 6
<212> TYPE: PRT
<213> ORGANISM: Artificial Sequence
<220> FEATURE:
<223> OTHER INFORMATION: Tag

<400> SEQUENCE: 30

His His His His His His
1               5


<210> SEQ ID NO 31
<211> LENGTH: 6
<212> TYPE: PRT
<213> ORGANISM: Artificial Sequence
<220> FEATURE:
<223> OTHER INFORMATION: Tag

<400> SEQUENCE: 31

His Glu His Glu His Glu
1               5
```

ANTI-HER2 AFFIBODY AND SWITCHABLE CHIMERIC ANTIGEN RECEPTOR USING SAME AS SWITCH MOLECULE

CROSS-REFERENCE TO RELATED APPLICATIONS

This application is a national phase application of PCT/KR2021/004793 filed on Apr. 16, 2021, which claims benefit of Korean Patent Application No. 10-2020-0047025 filed on Apr. 17, 2020. The entire disclosure of the applications identified in this paragraph is incorporated herein by references.

TECHNICAL FIELD

This invention was made with the support of the ministry of Trade, Industry and Energy under Project No. 20002893, which was conducted under the research project entitled "Development of HER2 Targeting Therapy for Ovarian Cancer Using Innovative Switchable CART Technology" within the project named "Project for Development of Core Technology in Bio Industry" by AbClon Inc. Under the management of the Korea Evaluation Institute of industrial Technology, from Oct. 1, 2018 to Jun. 30, 2021.

The present disclosure relates to an anti-HER2 affibody and a switchable chimeric antigen receptor using same as a switch molecule.

BACKGROUND ART

In spite of impressive success in early-stage clinical trials, conventional CAR-T cells have limitations associated with the lack of control over their activation and expansion in vivo. For example, CAR-T cells undergo rapid proliferation up to $10^4$-fold expansion upon encountering antigen-positive cells in the patient, which has resulted in serious cases of tumor lysis syndrome (TLS) and fatal cytokine release syndrome (CRS). Additional complications may be caused by the persistent on-target activity of CAR-T cells. In the case of CART-19, for example, engineered T cells indiscriminately kill malignant and normal B cells, leading to long-term B-cell aplasia. Finally, the fixed antigen-specificity of conventional CAR-T cells precludes the targeting of antigen-loss escape mutants, which has recently been shown to be a source of relapse in up to 10% of all patients undergoing CART-19 therapy. Thus, there is an increasing need for the development of a switch molecule that can control the activity of CAR-T cells when significant toxicity occurs in order to improve the stability of CAR-T cells and which can mediate interaction between CAR-T cells and target cells.

Human Epidermal Growth Factor Receptor 2 (HER2, also referred to as "HER2/neu" or "ErbB-2") is a 185 kDa transmembrane receptor belonging to the epidermal growth factor receptor family. HER2 gene amplification and protein overexpression play pivotal roles in the pathogenesis and progression of many types of cancer. HER2 is overexpressed in 25-30% of breast, 15-35% of gastric, and 7-38% of ovarian cancers and is correlated with poor survival. HER2 protein has consequently emerged in recent years as an important predictive biomarker and target of cancer therapy. Homo- or heterodimerization with other members of its family prompts activation of the intracellular tyrosine kinase domain and triggers cell survival and proliferation mediated through MAPK and Akt signaling pathways. Available HER2-targeted therapies in the clinic include receptor dimerization-preventing antibodies, such as trastuzumab (Herceptin, Genentech) and pertuzumab (Perjeta, Genentech), antibody-drug conjugates, such as T-DM1 (Kadcyla, Genentech), or small molecule inhibitors targeting the tyrosine-kinase domain (e.g., lapatinib, Tyverb, GlaxoSmithKline; a dual HER2 and EGFR inhibitor).

Many papers and patent documents are referenced and cited throughout this description. The disclosures of the cited papers and patent documents are incorporated herein by reference in their entireties to better understand the state of the art to which the present disclosure pertains and the content of the present disclosure.

[Patent Document]

PCT International Publication WO 2012-096760 A1 (Jul. 19, 2012).

SUMMARY

Technical Problem

Leading to the present disclosure, intensive and thorough research, conducted by the present inventors, into the development of a chimeric antigen receptor capable of treating HER2-expressing cancer, resulted in the finding that when applied together with a chimeric antigen receptor targeting cotinine, a cotinine-conjugated anti-HER2 affibody serving as a switch molecule reacts with HER2-expressing cancer cells to induce the activation of immune cells.

Therefore, an aspect of the present disclosure is to provide a novel anti-HER2 affibody.

Another aspect of the present disclosure is to provide a switch molecule comprising a cotinine-conjugated anti-HER2 affibody.

A further aspect of the present disclosure is to provide a switchable chimeric antigen receptor comprising the switch molecule and a chimeric antigen receptor targeting the switch molecule.

Solution to Problem

According to an aspect thereof, the present disclosure provides an anti-HER2 affibody including the amino acid sequence represented by the following General Formula:

General Formula (SEQ ID NO: 24)

$VDNKFNKEX_9X_{10}X_{11}AYWEIX_{17}X_{18}LPNLNX_{24}X_{25}QX_{27}X_{28}AFI$ $X_{32}X_{33}LX_{35}DDPSQSANLLAEAKKLNDAQAPK$

In the General Formula, an amino acid residue expressed in an Xy format is involved in binding specifically to a target antigen of the polypeptide consisting of the amino acid sequence and refer to an amino acid at position y in the amino acid sequence and may be selected from all the 20 naturally occurring amino acid residues.

In the description, the amino acid residues which are not expressed in the Xy format are referred to as scaffold amino acids or scaffold. Being responsible for structural stability for the polypeptide or polypeptide complex of the present disclosure, the scaffold amino acids are discriminated from the random amino acids which are expressed in the Xy format and endow binding affinity for a target antigen of the polypeptide of the present disclosure.

In the General Formula, (i) $X_9X_{10}X_{11}$ is LRV, $X_{17}X_{18}$ is VK, $X_{24}X_{25}$ is PY, PP, or PK, $X_{27}X_{28}$ is SR or IT, $X_{32}X_{33}$ is RS or KQ, and $X_{35}$ is Y;

(ii) $X_9X_{10}X_{11}$ is LRG, $X_{17}X_{18}$ is TS, $X_{24}X_{25}$ is HS, $X_{27}X_{28}$ is IT, $X_{32}X_{33}$ is VS, and $X_{35}$ is Y;

(iii) $X_9X_{10}X_{11}$ is MRD, $X_{17}X_{18}$ is VR, $X_{24}X_{25}$ is RI or PP, $X_{27}X_{28}$ is ST or SV, $X_{32}X_{33}$ is RS or RQ, and $X_{35}$ is Y;

(iv) $X_9X_{10}X_{11}$ is YML, $X_{17}X_{18}$ is VK, $X_{24}X_{25}$ is YP, $X_{27}X_{28}$ is QH, $X_{32}X_{33}$ is RS, and $X_{35}$ is F; or (v) $X_9X_{10}X_{11}$ is INK, $X_{17}X_{18}$ is IS, $X_{24}X_{25}$ is KE, $X_{27}X_{28}$ is HH, $X_{32}X_{33}$ is HS, and $X_{35}$ is Y.

In an embodiment of the present disclosure, $X_{35}$ is Y.

In an embodiment of the present disclosure, $X_{10}$ is R.

In an embodiment of the present disclosure, $X_{17}$ is V.

In an embodiment of the present disclosure, $X_{24}$ is P.

In an embodiment of the present disclosure, the anti-HER2 affibody includes an amino acid sequence of any one of SEQ ID NOS: 1 to 8.

As used herein, the term "affibody molecule" (Affibody®) refers to a small protein composed of 58 amino acid residues based on the Z domain, which is an affinity site for IgG in Protein A from *Staphylococcus aureus*. In this disclosure, "affibody" is also represented by "Z body" or "Zb". In the amino acid sequence of the affibody molecule, 13 amino acids that form the binding surface with IgG can bind to various target antigens depending on the amino acid sequence thereof and can be randomly arranged to construct libraries. Similar to antibodies, affibody molecules capable of binding to various target antigens can be screened from libraries through screening methods, such as phage display and yeast two hybrid (Y2H). When administered into the human body, the affibody molecules are systemically diffused and quickly removed through renal clearance because they have a very small molecular weight of 6 kDa, compared to IgG, which generally has a molecular weight of 150 kDa. Therefore, affibody molecules are mainly applied to the research and development of diagnostic specimens (Goldstein R et al., 2013, Expert Rev Anticancer Ther.). Affibody molecules have also been developed in the form of double antibodies binding to IgG (Yu F et al., 2014, MAbs). PCT Publication No. WO95/19374 discloses first-generation Z domain variant-based polypeptide scaffolds and PCT Publication No. WO2009/080811 discloses second-generation Z domain variant-based polypeptide scaffolds.

Provided according to another aspect of the present disclosure is a nucleic acid molecule including a nucleotide sequence coding for the anti-HER2 affibody.

In an embodiment of the present disclosure, the nucleotide sequence coding for the anti-HER2 affibody of the present disclosure may be any nucleotide sequence as long as it encodes the amino acid sequence of the anti-HER2 affibody. It should be understood to a person skilled in the art that the nucleotide sequence coding for the anti-HER2 affibody of the present disclosure is not limited to a specific nucleotide sequence. The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e.g., due to the degeneracy of codons, the number of codons for arginine or serine being six), or codons containing biologically equivalent amino acids.

As used herein, the term "nucleic acid" is intended to comprehensively encompass DNA (gDNA and cDNA) and RNA molecules, and nucleotides as basic constituent units in the nucleic acid molecules include naturally occurring nucleotides, and analogues with modified sugars or bases (Scheit, Nucleotide Analogs, John Wiley, New York (1980); Uhlman and Peyman, Chemical Reviews, 90:543-584 (1990)).

Considering the above-described mutation having biologically equivalent activity, it should be construed that the nucleic acid molecules of the present disclosure encoding the amino acid sequences responsible for the constitution of the anti-HER2 affibody also include sequences showing substantial identity therewith. The substantial identity refers to a sequence showing at least 60%, more preferably at least 70%, still more preferably at least 80%, still more preferably at least 90% nucleotide, and most specifically at least 95% identity when the sequence of the present disclosure and any other sequence are correspondingly aligned as much as possible and the aligned sequence is analyzed using algorithms commonly used in the art. Methods of alignment for sequence comparison are known in the art. Various methods and algorithms for alignment are disclosed in Smith and Waterman, Adv. Appl. Math. 2:482 (1981); Needleman and Wunsch, J. Mol. Bio. 48:443 (1970); Pearson and Lipman, Methods in Mol. Biol. 24: 307-31 (1988); Higgins and Sharp, Gene 73:237-44 (1988); Higgins and Sharp, CABIOS 5:151-3 (1989); Corpet et al., Nuc. Acids Res. 16:10881-90 (1988); Huang et al., Comp. Appl. BioSci. 8:155-65 (1992) and Pearson et al., Meth. Mol. Biol. 24:307-31 (1994), but are not limited thereto.

According to a further aspect thereof, the present disclosure provides a recombinant vector carrying a nucleic acid molecule coding for the anti-HER2 affibody.

The term "vector", as used herein, refers to a means for expressing a gene of interest in a host cell. Examples of the vector available herein include: plasmid vectors; cosmid vectors; and viral vectors such as bacteriophage vectors, adenovirus vectors, retrovirus vectors, and adeno-associated virus vectors.

According to an exemplary embodiment of the present disclosure, the nucleic acid molecule encoding the affibody is operatively linked to a promoter in the vector.

As used herein, the term "operatively linked" refers to a functional linkage between a nucleic acid expression control sequence (e.g., a promoter, a signal sequence, or an array of transcription regulation factor binding sites) and another nucleic acid sequence, whereby the control sequence controls the transcription and/or translation of the nucleic acid sequence.

The recombinant vector system of the present disclosure can be constructed by various methods known in the art, and specific methods thereof are disclosed in Sambrook, et al., Molecular Cloning, A Laboratory Manual, Cold Spring Harbor Laboratory Press (2001), the teachings of which are incorporated herein by reference.

The vector of the present disclosure may be typically constructed as a vector for gene cloning or a vector for protein expression. In addition, the vector of the present disclosure may be constructed by using prokaryotic or eukaryotic cells as a host.

For example, when the vector of the present disclosure is an expression vector, with an eukaryotic cell serving as a host cell, promoters derived from genomes of mammalian cells (e.g., metallothionein promoter, beta-actin promoter, human hemoglobin promoter, and human muscle creatinine promoter) or promoters derived from mammalian viruses (e.g., adenovirus late promoter, vaccinia virus, 7.5K promoter, SV40 promoter, cytomegalovirus (CMV) promoter, HSV tk promoter, mouse mammary tumor virus (MMTV) promoter, HIV LTR promoter, Moloney virus promoter, Epstein Barr Virus promoter, Rous Sarcoma Virus promoter) may be available. Generally, the vectors include a polyadenylate sequence as a transcriptional termination sequence.

The vector of the present disclosure may be fused to another sequence to facilitate the purification of a polypeptide expressed therefrom. Examples of the sequence to be used for the fusion include glutathione S-transferase (Pharmacia, USA), maltose binding protein (NEB, USA), FLAG (IBI, USA), and 6× His (hexahistidine; Quiagen, USA).

The vector of the present disclosure includes, as a selective marker, an antibiotic-resistant gene that is ordinarily used in the art, and may include resistant genes against ampicillin, gentamycin, carbenicillin, chloramphenicol, streptomycin, kanamycin, geneticin, neomycin, and tetracycline.

According to another aspect thereof, the present disclosure provides a host cell transformed with the recombinant vector.

So long as it is known in the art to stabilize the vector of the present disclosure and continually clone and express the vector, any host cell may be employed in the present disclosure. Examples of the eukaryotic host cells suitable for the vector include monkey kidney cells 7 (COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

As used herein, the term "transformed", "transduced", or "transinfected" refers to pertaining to a process for delivering or introducing an exogenous nucleic acid into a host cell. A "transformed", "transduced", or "transfected" cell is one which has been transformed, transduced, or transfected with an exogenous nucleic acid. The cell includes the primary subject cell and its progenies resulting from passages.

According to another aspect thereof, the present disclosure provides a switch molecule for activating chimeric antigen receptor-effector cells, the switch molecule comprising a cotinine-conjugated anti-HER2 affibody represented by the following General Formula:

General Formula (SEQ ID NO: 24)

$VDNKFNKEX_9X_{10}X_{11}AYWEIX_{17}X_{18}LPNLNX_{24}X_{25}QX_{27}X_{28}AFI$ $X_{32}X_{33}LX_{35}DDPSQSANLLAEAKKLNDAQAPK$ wherein, (i) $X_9X_{10}X_{11}$ is LRV, $X_{17}X_{18}$ is VK, $X_{24}X_{25}$ is PY, PP, or PK, $X_{27}X_{28}$ is SR or IT, $X_{32}X_{33}$ is RS or KQ, and $X_{35}$ is Y;

(ii) $X_9X_{10}X_{11}$ is LRG, $X_{17}X_{18}$ is TS, $X_{24}X_{25}$ is HS, $X_{27}X_{28}$ is IT, $X_{32}X_{33}$ is VS, and $X_{35}$ is Y;

(iii) $X_9X_{10}X_{11}$ is MRD, $X_{17}X_{18}$ is VR, $X_{24}X_{25}$ is RI or PP, $X_{27}X_{28}$ is ST or SV, $X_{32}X_{33}$ is RS or RQ, and $X_{35}$ is Y;

(iv) $X_9X_{10}X_{11}$ is YML, $X_{17}X_{18}$ is VK, $X_{24}X_{25}$ is YP, $X_{27}X_{28}$ is QH, $X_{32}X_{33}$ is RS, and $X_{35}$ is F; or (v) $X_9X_{10}X_{11}$ is INK, $X_{17}X_{18}$ is IS, $X_{24}X_{25}$ is KE, $X_{27}X_{28}$ is HH, $X_{32}X_{33}$ is HS, and $X_{35}$ is Y.

In an embodiment of the present disclosure, $X_{35}$ is Y.

In an embodiment of the present disclosure, $X_{10}$ is R.

In an embodiment of the present disclosure, $X_{17}$ is V.

In an embodiment of the present disclosure, $X_{24}$ is P.

In an embodiment of the present disclosure, the anti-HER2 affibody includes an amino acid sequence of any one of SEQ ID NOS: 1 to 8.

Cotinine is the predominant metabolite of nicotine and has the structure of Chemical Formula 1:

[Chemical Formula 1]

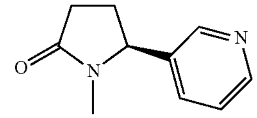

As used herein, the term "switch molecule" refers to an adaptor molecule in a T cell therapy product using the chimeric antigen receptor, that is, called CAR-T cell therapy product, which separates the target recognition domain and intracellular signaling domain of CAR from each other and mediates the same. Switch molecules allow CAR-expressing cells to be redirected to target heterogeneous or resistant tumors or to be reduced in terms of activity by dosage thereof when side effects are generated due to excessive activation of the CAR-expressing cells (Cao et al., Angew Chem Int Ed Engl. 2016 Jun. 20; 55(26): 7520-7524).

In an embodiment of the present disclosure, the activation of the effector cell results in cytotoxicity against a target cell, cytokine secretion, or a combination thereof.

In an embodiment of the present disclosure, the effector cell is selected from the group consisting of a dendritic cell, a killer dendritic cell, a mast cell, a natural killer cell, a B lymphocyte, a T lymphocyte, a macrophage, and a precursor cell thereof, but with no limitations thereto.

The anti-HER2 affibody and cotinine, which are responsible for the constitution of the switch molecule in the present disclosure, are coupled to each other by chemical conjugation.

The chemical conjugation may be achieved by a chemical linker. Examples of the chemical linker include, but are not limited to, EDC (1-ethyl-3-(3-dimethylaminopropyl)carbodiimide hydrochloride), DCC (dicyclohexyl carbodiimide), NHS (N-hydroxysuccinimide), Sulfo-NHS (N-hydroxysulfosuccinimide), imidoester-based linkers, and Sulfo-SMCC (sulfosuccinimidyl 4-(N-maleimidomethyl)cyclohexane-1-carboxylate). Any chemical linker that is typically used in the art may be employed without limitations.

In an embodiment of the present disclosure, the anti-HER2 affibody in the switch molecule may be conjugated with one or more, two or more, or three or more cotinine molecules.

In an exemplary embodiment of the present disclosure, cotinine may be conjugated to the N- or C-terminus of the polypeptide of the anti-HER2 affibody.

In another exemplary embodiment of the present disclosure, cotinine may be conjugated to both the N- and C-terminus of the polypeptide of the anti-HER2 affibody.

In an embodiment of the present disclosure, the anti-HER2 affibody and cotinine, which are responsible for the constitution of the switch molecule, are connected to each other directly or indirectly via a linker.

A person skilled in the art could conceive that a linker may be used between functional moieties to be usually fused in the production of a fusion protein and would understand that there are different kinds of linkers having different characteristics, for example, a flexible amino acid linker, a non-flexible linker, and a cleavable amino acid linker. The linkers have been used for the purpose of increasing expression levels, improving biological activity, and enabling targeting, or modifying pharmacokinetics of the fusion protein, or in order to increase stability and improve folding property of the fusion protein.

Therefore, according to a specific embodiment of the present disclosure, the switch molecule may further comprise at least one linker, for example, at least one linker selected from flexible amino acid linkers, non-flexible linkers, and cleavable amino acid linkers. According to an exemplary embodiment of the present disclosure, the linker is arranged between the anti-HER2 affibody and the cotinine.

In this regard, the linker may include an amino acid sequence represented by general formula $(G_nS_m)_p$ or $(S_mG_n)_p$, wherein n, m, and p each independently satisfies the following conditions:

n is an integer of 1 to 7;

m is an integer of 0 to 7;

with a proviso that a sum of n and m is an integer of 8 or less; and p is an integer of 1 to 7.

In the linker according to an exemplary embodiment of the present disclosure, n=1 to 5 and m=0 to 5. In the linker according to a more exemplary embodiment of the present disclosure, n=4 and m=1. According to a further more exemplary embodiment of the present disclosure, the linker is $(G_4S)_3$ (SEQ ID NO: 25) or $(S_4G)_3$ (SEQ ID NO: 26). According to another embodiment of the present disclosure, the linker is GGGGS (SEQ ID NO: 27).

According to a further embodiment of the present disclosure, the linker is VDGS (SEQ ID NO: 28). According to yet another embodiment of the present disclosure, the linker is ASGS (SEQ ID NO: 29).

Here, polypeptides or fusion proteins expressed in this disclosure, including the anti-HER2 affibody as a component of the switch molecule, may contain at least one additional amino acid at the C-terminus and/or N-terminus thereof. The additional amino acid residues may be individually or collectively added for the purpose of improving, for example, productivity, purification, in vivo or in vitro stabilization, coupling with the complex, or detection. By way of example, a cysteine residue may be added to the C-terminus and/or N-terminus of the polypeptide or fusion protein. The additional amino acid residue may provide a "tag" for purification or polypeptide detection and, for example, for interaction with an antibody specific therefor. In this regard, $His_6$ tag (SEQ ID NO: 30), $(HisGlu)_3$ tag ("HEHEHE" tag) (SEQ ID NO: 31), "myc" (c-myc) tag, or "FLAG" tag may be provided for immobilized metal affinity chromatography (IMAC).

According to another aspect thereof, the present disclosure provides an immunotherapeutic pharmaceutical composition comprising: the switch molecule; and a pharmaceutically acceptable carrier.

The term "immunotherapy", as used herein, refers to the artificial stimulation of the immune system to treat cancer. Immunotherapy can be either active or passive. Active immunotherapy includes i) cancer vaccine therapy in which cancer cells or a material produced from cancer cells are injected to the human body to boost the immune system, and ii) immune-modulating therapy in which immune-modulating agents such as cytokines (interferon, interleukin, etc.), growth factors, and so on are administered to activate specific leukocytes. Within passive immunotherapy are included the administration of therapeutic antibodies binding to specific cancer cells, and immune cell therapy. Examples of immune cell therapy include dendritic cell vaccine therapy, CAR-T (chimeric antigen receptor T cell) therapy, natural killer (NK) cell therapy, cytotoxic T lymphocyte (CTL) therapy, and adoptive cell transfer, but are not limited thereto. Herein, immune therapy refers mainly to the immune cell therapy.

Since the switch molecule of the present disclosure contains an affibody specifically binding to HER2 antigen, the pharmaceutical composition comprising the switch molecule of the present disclosure as an active ingredient can be applied to the treatment of human and animal diseases associated with cells expressing HER2. In detail, the diseases include breast cancer, ovarian cancer, colorectal cancer, and endometrial cancer, but are not limited thereto.

So long as it is typically used for the pharmaceutical composition of the present disclosure, any pharmaceutically acceptable carrier may be contained in the pharmaceutical composition of the present disclosure. Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto.

The pharmaceutical composition of the present disclosure may further comprise a lubricant, a wetting agent, a sweetener, a flavorant, an emulsifier, a suspending agent, a preservative, and the like in addition to the above ingredients. With regard to suitable pharmaceutically acceptable carriers and preparations, reference may be made to Remington's Pharmaceutical Sciences ($19^{th}$ ed., 1995).

The pharmaceutical composition of the present disclosure may be administered orally or parenterally, for example, intravenously, subcutaneously, intramuscularly, intraperitoneally, intrasternally, intratumorally, topically, intranasally, intracerebrally, intracranially, intrapulmonarily, and rectally, but without limitations thereto.

Appropriate doses of the pharmaceutical composition of the present disclosure vary depending on various factors including a formulating method, a manner of administration, patient's age, body weight, sex, and morbidity, food, a time of administration, a route of administration, an excretion rate, and response sensitivity. An ordinarily skilled practitioner can easily determine and prescribe an effective dose for desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, amelioration, or eradication of a disease condition.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure belongs. Here, the formulation may be in the form of a solution in an oily or aqueous medium, a suspension, an emulsion, an extract, a pulvis, a suppository, a powder, a granule, a tablet, or a capsule, and may further contain a dispersant or a stabilizer. In addition to the switch molecule, the pharmaceutical composition of the present disclosure may further comprise other pharmaceutically active agents or drugs, for example, chemotherapeutic agents such as asparaginase, busulfane, carboplatin, cisplatin, daunorubicin, doxorubicin, fluorouracil, gemcitabine, hydroxyurea, methotrexate, paclitaxel, rituximab, vinblastine, vincristine, and the like.

In accordance with another aspect thereof, the present disclosure provides a switchable chimeric antigen report comprising:

(a) the switch molecule comprising a cotinine-conjugated anti-HER2 affibody; and (b) a chimeric antigen receptor comprising:

i) an extracellular domain including an antibody targeting the switch molecule, or an antigen binding fragment thereof;

ii) a transmembrane domain; and iii) an intracellular signaling domain.

According to a further still aspect thereof, the present disclosure provides a CAR-effector cell therapeutic system comprising: the switch molecule of the present disclosure; and the chimeric antigen receptor targeting the switch molecule of the present disclosure.

When used, the CAR-effector cell therapeutic system according to the present disclosure can treat cancer (e.g., HER2 expression-associated cell cancer) by administering to a patient in need thereof the switch molecule binding specifically to a surface antigen (e.g., HER2) on a specific cancer cell and an effector cell (e.g., T cell, dendritic cell, NK cell, etc.) expressing a chimeric antigen receptor targeting the switch molecule.

The term "chimeric antigen receptor" (CAR), as used herein, refers to an artificially constructed hybrid protein (fusion protein) or polypeptide containing a target binding domain (e.g., single-chain variable fragment (scFv)) linked to an effector cell signaling domain or an effector cell activating domain (e.g., T-cell signaling or T-cell activating domain). Chimeric antigen receptors have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimer with endogenous T-cell receptor (TCR) alpha and beta chain.

The chimeric antigen receptor of the present disclosure is a switchable chimeric antigen receptor (sCAR). An extracellular domain in atypical classical chimeric antigen receptor contains an antibody or antigen-binding fragment targeting a specific antigen (e.g., a tumor associated antigen (TAA) such as a HER2 antigen, a CD19 antigen, etc.). However, the extracellular domain in the chimeric antigen receptor of the present disclosure targets the switch molecule (in detail, cotinine in the switch molecule).

In an embodiment of the present disclosure, the antibody or the antigen-binding fragment thereof in i) is an anti-cotinine antibody or an antigen-binding fragment thereof.

In an exemplary embodiment of the present disclosure, the anti-cotinine antibody or the antigen-binding fragment thereof includes HCDR1 of SEQ ID NO: 9, HCDR2 of SEQ ID NO: 10, HCDR3 of SEQ ID NO: 11, LCDR1 of SEQ ID NO: 12, LCDR2 of SEQ ID NO: 13, and LCDR3 of SEQ ID NO: 14, but are not limited thereto.

In an embodiment of the present disclosure, the transmembrane domain includes a transmembrane domain of a protein selected from the group consisting of the alpha, beta, or zeta chain of a T-cell receptor, CD27, CD28, CD3, epsilon, CD45, CD4, CD5, CD8 (CD8α), CD9, CD16, CD22, CD33, CD37, CD64, CD80, CD86, CD134, CD137, and CD154.

In an embodiment of the present disclosure, the intracellular signaling domain is an intracellular signaling domain found in stimulatory molecules and costimulatory molecules and is responsible for activating CAR-expressing cells.

Non-limiting examples of the intracellular signaling domain include TCR, CD3 zeta, CD3 gamma, CD3 delta, CD3 epsilon, CD86, typical FcR gamma, FcR beta (Fc epsilon Rib), CD79a, CD79b, Fc gamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that binds specifically to CD83, CDS, ICAM-1, GITR, BAFFR, HVEM(LIGHTR), SLAMF7, NKp80 (KLRF1), CD127, CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other costimulatory molecules described herein, any derivative, variant, or fragment thereof, any synthetic sequence of a co-stimulatory molecule that has the same functional capability, and any combination thereof.

According to an exemplary embodiment of the present disclosure, the intracellular signaling domain is a domain derived from the CD3 zeta chain.

According to an exemplary embodiment of the present disclosure, the intracellular signaling domain derived from the CD3 zeta chain includes the amino acid sequence encoded by the nucleotide sequence of SEQ ID NO: 23.

According to another exemplary embodiment of the present disclosure, the intracellular signaling domain further comprises a costimulatory molecule selected from the group consisting of OX40 (CD134), CD2, CD27, CD28, CDS, ICAM-1, LFA-1 (CD11a/CD18), and 4-1BB (CD137). The intracellular signaling domain may be obtained or derived from a singling molecule within other cells known in the art in addition to the aforementioned domain and may comprise the entirety or a fragment of the origin molecule thereof.

The transmembrane domain and intracellular signaling domain in the chimeric antigen receptor of the present disclosure may be included in one or more combinations of the transmembrane domains and intracellular signaling domains described above. For example, the chimeric antigen receptor of the present disclosure may include the hinge and transmembrane domain of CD8, the cytosolic region of CD137, and the intracellular signaling domain of CD3ζ. In another instance, the chimeric antigen receptor of the present disclosure may include the transmembrane domain of CD8α and the intracellular signaling domains of CD28 and CD3ζ.

In an embodiment of the present disclosure, the chimeric antigen receptor may optionally further comprise a leader sequence (LS). The leader sequence is positioned at the amino terminal (N-terminal) of the recombinant polypeptide responsible for the constitution of the chimeric antigen receptor. The leader sequence is cleaved as the chimeric antigen receptor undergoes intracellular processing and localization into the cell membrane.

In an exemplary embodiment of the present disclosure, the leader sequence includes the amino acid sequence encoded by the nucleotide sequence of SEQ ID NO: 20.

The HER2-binding domain of the chimeric antigen receptor according to the present disclosure is linked to the transmembrane domain via a hinge domain (or spacer).

According to another embodiment of the present disclosure, the hinge domain is a hinge derived from IgG1, IgG2, IgG4, or IgD, a hinge derived from CD8 or CD28, an extracellular domain (ECD) derived from CD28, or a combination thereof.

In an exemplary embodiment of the present disclosure, the hinge domain and the transmembrane domain include the amino acid sequence encoded by the nucleotide sequence of SEQ ID NO: 21.

The term "antibody", as used herein, refers to an antibody specifically binding to a specific antigen and is intended to encompass not only a whole antibody but also an antigen-binding fragment thereof. A whole antibody includes two full-length light chains and two full-length heavy chains wherein the light chains are linked respectively to the heavy chains via disulfide bonds. The heavy chain constant regions are divided into isotypes of gamma (γ), mu (μ), alpha (α), delta (δ), and epsilon (ε), which are further divided into the subclasses gamma 1 (γ1), gamma 2 (γ2), gamma 3 (γ3), gamma 4 (γ4), alpha 1 (α1), and alpha 2 (α2). The light chain constant region is divided into kappa (κ) and lambda (λ) types (Cellular and Molecular Immunology, Wonsiewicz, M. J., Ed., Chapter 45, pp. 41-50, W. B. Saunders Co. Philadelphia, PA (1991); Nisonoff, A., Introduction to Molecular Immunology, 2nd Ed., Chapter 4, pp. 45-65, Sinauer Associates, Inc., Sunderland, MA (1984)).

Herein, the antibody includes an antibody selected from the group consisting of a monoclonal antibody, a polyclonal antibody, a synthetic antibody, a human antibody, a humanized antibody, a single domain antibody, and a single-chain variable fragment.

As used herein, the term "antigen-binding fragment" refers to a fragment having an antigen binding activity and is intended to encompass Fab, F(ab'), F(ab')2, and Fv. Of the antibody fragments, Fab (fragment antigen binding) is composed of one variable domain of each of the heavy and the light chain, one constant domain of the light chain, and the first constant domain (CH1) of the heavy chain, with one antigen-binding site retained therein. Fab' is different from Fab in that the former retains a hinge region which comprises at least one cysteine residue at C-terminal of the heavy chain CH1 domain. F(ab')2 antibody is produced by forming a disulfide bond between cysteine residues in the hinge region of Fab'. Fv is a minimal antibody fragment composed only of variable regions of a heavy and a light chain and may be produced by a recombinant technology as disclosed in PCT International Patent Publication Nos. WO 88/10649, WO 88/106630, WO 88/07085, WO 88/07086, and WO 88/09344. In a two-chain Fv, variable regions of a light and a heavy chain are linked by a non-covalent bond. In a single-chin variable fragment (scFv), variable regions of a light and a heavy chain are linked by a covalent bond through a peptide linker or it may form a dimer structure like a two chain Fv through a direct linkage at the C-terminal. These antibody fragments are obtained through a proteinase treatment (for example, a whole antibody may be digested with a papain to obtain Fab or with a pepsin to obtain F(ab')2). Alternatively, a recombinant DNA technology may be employed to fabricate the antibody fragments.

The term "heavy chain", as used herein, refers to a full-length chain comprising three constant regions CH1, CH2, and CH3 and one variable region VH comprising an amino acid sequence which is sufficient for conferring specificity to an antigen as well as fragments thereof. Also, the term "light chain", as used herein, refers to a full-length chain comprising one constant region CL and one variable region VL comprising an amino acid sequence which is sufficient for conferring specificity to an antigen as well as fragment thereof.

As used herein, the term "complementarity determining region" (CDR) refers to an amino acid sequence of a hypervariable region within the heavy and light chain variable domains of an immunoglobulin (Kabat et al., Sequences of Proteins of Immunological Interest, 4th Ed., U.S. Department of Health and Human Services, National Institutes of Health (1987)). There are three CDRs in each of the heavy chain (CDRH1, CDRH2, and CDRH3) and the light chain (CDRL1, CDRL2, and CDRL3). The CDRs provide major contact residues for binding to an antigen or an epitope.

By "humanized antibody" are meant chimeric immunoglobulins, immunoglobulin chains or fragments thereof (such as Fv, Fab, Fab', F(ab')2 or other antigen-binding sub-sequences of antibodies) which contain minimal sequence derived from non-human immunoglobulins of non-human (e.g., murine) antibodies. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody will optimally also comprise at least a portion of an immunoglobulin constant region (Fc), typically that of a human immunoglobulin.

According to another aspect thereof, the present disclosure provides a nucleic acid molecule comprising a nucleotide sequence coding for the polypeptide of the chimeric antigen receptor.

According to a further aspect thereof, the present disclosure provides a recombinant vector carrying a nucleic acid molecule coding for the polypeptide of the chimeric antigen receptor.

The term "vector", as used herein, is intended to encompass a transfer vector and an expression vector.

The term "transfer vector", as used herein, refers to a composition of matter which comprises an isolated nucleic acid and which can be used to deliver the isolated nucleic acid into the interior of a cell. Examples of the transfer vector include, but are not limited to, linear polynucleotides, polynucleotides associated with ionic or amphiphilic compounds, plasmids, and viruses. More specifically, the transfer vector includes an autonomously replicating plasmid or virus. The term should also be construed to further include non-plasmid and non-viral compounds which facilitate the transfer of nucleic acid into cells, such as, polylysine compounds or liposomes. Examples of viral transfer vectors include, but are not limited to, adenoviral vectors, adeno-associated virus vectors, retroviral vectors, and lentiviral vectors.

In an embodiment of the present disclosure, the vector is a lentiviral vector. In an exemplary embodiment of the present disclosure, the vector further comprises a promoter. The promoter may be, for example, an EF-1alpha promoter, but without limitations thereto.

In an exemplary embodiment of the present disclosure, the EF-1alpha promoter includes the nucleotide sequence of SEQ ID NO: 19.

According to another embodiment of the present disclosure, the vector may be a retroviral vector. Retroviruses provide a convenient platform for gene delivery systems. A gene selected for gene delivery can be inserted into a retroviral vector and packaged in retroviral particles. The recombinant retroviral virus can then be delivered to target host cells either in vivo or in vitro. A number of retroviral vectors are known in the art.

According to another aspect thereof, the present disclosure provides an effector cell expressing the chimeric antigen receptor. The chimeric antigen receptor targets the switch molecule.

According to an embodiment of the present disclosure, the effector cell is selected from the group consisting of a dendritic cell, a killer dendritic cell, a mast cell, a natural killer cell, a B lymphocyte, a T lymphocyte, a macrophage, and precursor cells thereof.

According to an exemplary embodiment of the present disclosure, the T lymphocyte may be selected from the group consisting of an inflammatory T lymphocyte, a cytotoxic T lymphocyte, a regulatory T lymphocyte, or a helper T lymphocyte.

The effector cells in the present disclosure include a population of autologous or allogeneic cells. In other words, the effector cells include a population of autologous or allogeneic cells expressing the chimeric antigen receptor of the present disclosure.

As used herein, the term "autologous" refers to any material derived from the same individual to whom it is later to be re-introduced. The term "allogeneic" refers to any material derived from a different animal of the same species as the individual to whom the material is introduced.

In addition, according to an embodiment of the present disclosure, the effector cells include a population of the cells transfected or transduced with a vector carrying a nucleic acid molecule coding for the chimeric antigen receptor of the present disclosure. The transfection or transduction may be achieved using various means known in the art as described in the foregoing, without limitations.

Therefore, according to an exemplary embodiment of the present disclosure, after being transferred into an effector cell, e.g., T lymphocyte or natural killer cell, the nucleic acid molecule encoding a chimeric antigen receptor according to the present disclosure is transcribed into mRNA from which the chimeric antigen receptor is translated and expressed on the surface of the effector cell.

As will be proven in the following Example section, the switch molecule including a cotinine-conjugated anti-HER2 affibody and the effector cell expressing a chimeric antigen receptor targeting the cotinine of the switch molecule according to the present disclosure effectively kill the cancer cell line SKOV3 (ovarian cancer cell line) that expresses HER2 on the surface thereof. Therefore, the anti-HER2 switch molecule and the effector cell expressing a chimeric antigen receptor targeting the switch molecule according to the present disclosure can be advantageously used as active ingredients in a pharmaceutical composition for treatment of HER2-expressing carcinoma.

The pharmaceutical composition of the present disclosure may comprise a CAR-expressing effector cell, e.g., a plurality of CAR-expressing effector cells, as described herein, in combination with one or more pharmaceutically or physiologically acceptable carriers, diluents, or excipients. The pharmaceutical composition may comprise buffers such as neutral buffered saline, phosphate buffered saline and the like; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives. In an embodiment, the pharmaceutical composition according to an embodiment of the present disclosure may be formulated for intravenous administration.

The pharmaceutical composition of the present disclosure may be administered orally or parenterally, for example, by intravenous injection, subcutaneous injection, intramuscular injection, intraperitoneal injection, intratumoral injection, intracerebral injection, intracranial injection, intrapulmonary administration, and rectal administration, but without limitations thereto.

The pharmaceutical composition comprising effector cells in accordance with the present disclosure is administered to a patient by intradermal or subcutaneous injection. In an embodiment, the pharmaceutical composition of the present disclosure is administered by intravenous injection. In another embodiment, the pharmaceutical composition may be administered directly into tumors, lymph nodes, or sites of infection.

Subjects in need of the present disclosure may undergo standard treatment with high dose chemotherapy. In an embodiment of the present disclosure, a subject in need of the present disclosure may be administered the proliferated CAR-T cells of the present disclosure subsequently to or simultaneously with the chemotherapy. In another embodiment, the proliferated CAR-T cells are administered prior to or subsequent to surgery.

When "an immunologically effective amount", "an anti-tumor effective amount", "a tumor-inhibiting effective amount", or "a therapeutic amount" is indicated, the precise amount of the compositions of the present disclosure to be administered can be determined by a physician with consideration of various factors including formulation methods, administration modalities, patient's age, weight, sex, and morbidity, a diet, administration time, administration routes, excretion rates, and response sensitivity. An ordinarily skilled practitioner can easily determine and prescribe an effective dose for desired treatment or prevention. Suitable dosages will be determined by clinical trials. As used herein, the term "treatment" refers to a reduction, suppression, amelioration, or eradication of a disease condition. The term "anti-tumor" effect as used herein, refers to a biological effect which can be manifested by a decrease in tumor volume, a decrease in the number of tumor cells, a decrease in the number of metastases, an increase in life expectancy, a decrease in the proliferation of tumor cells, a decrease in the survival of tumor cells, or amelioration of various physiological symptoms associated with the cancerous condition, but without limitations thereto.

It can generally be stated that a pharmaceutical composition comprising the T cells described herein may be administered at a dosage of $10^4$ to $10^9$ cells/kg body weight, in some instances $10^5$ to $10^6$ cells/kg body weight (including all integer values within those ranges). T cell compositions may also be administered multiple times at these dosages. The cells can be administered by using infusion techniques that are commonly known in immunotherapy (see, e.g., Rosenberg et al., New Eng. J. of Med. 319: 1676, 1988).

In addition to the active ingredients, the pharmaceutical composition of the present disclosure may employ other pharmaceutically active drug and therapies in combination. The term "combination" means relating to administering concurrently or together. The CAR-expressing effector cell described herein and the at least one additional therapeutic agent can be administered simultaneously, in the same or in separate compositions, or sequentially. For sequential administration, the CAR-expressing effector cell described herein can be administered first, and the additional agent can be administered second, or the order of administration can be reversed.

Within the scope of the therapeutic agent available in combination with the pharmaceutical composition of the present disclosure, one or more chemotherapeutic agents (e.g., asparaginase, busulfan, carboplatin, cisplatin, daunorubicin, doxorubicin, fluorouracil, gemcitabine, hydroxyurea, methotrexate, paclitaxel, rituximab, vinblastine, bincristine, etc.), one or more target therapeutic agents (e.g., bevacizumab, olaparib, etc.), and PD-1/PD-L1-specific immune checkpoint inhibitors (e.g., Opdivo, Keytruda, etc.) fall, but without limitations thereto.

According to another aspect thereof, the present disclosure provides a method for treatment of a HER2 expression-associated disease, the method comprising a step of administering: an effector cell expressing the chimeric antigen receptor; and a switch molecule binding to the chimeric antigen receptor to a subject in need thereof.

When generated during a procedure for treating a tumor- or cancer-disease or condition with CAR-T, a mutation (e.g., mutation of HER2 antigen) in a cell surface molecule on cancer cells hinders preexisting CARs from recognizing the mutated cancer cells, thus reducing therapeutic effects or making it impossible to treat the disease or condition. In this regard, if further administered to the subject, a novel switch molecule that targets a surface molecule on the mutated cells may exhibit a persistent therapeutic effect, in lieu of the previously admitted switch molecule.

According to a further aspect thereof, the present disclosure provides a method for restraining activity of an effector cell expressing the chimeric antigen receptor (CAR-effector cell) in a subject in need thereof, the method comprising the steps of: (a) administering to the subject the CAR-effector cell and the switch molecule binding to the chimeric antigen receptor; and (b) additionally administering to the subject either at least one switch molecule (e.g., cotinine-conjugated anti-EGFR) different from the previously administered switch molecule and binding to a cell surface molecule on the target cell or a targeting moiety-lacking switch molecule (e.g., cotinine only).

When generated in the course of treating a tumor- or cancer-associated disease or condition with CAR-T, the undue activation of CAR-T cells may cause a complication such as tumor lysis syndrome (TLS), cytokine release syndrome (CRS), etc., which are fetal to the patient. In the CAR-effector cell therapeutic system employing the switch molecule according to the present disclosure, the CAR-effector cell recognizes a cell surface molecule on cancer cells not directly, but indirectly via the switch molecule targeted by CAR. Hence, when either one or more switch molecules different from the previously administered switch molecule and binding to a cell surface molecule on target cells or a targeting moiety-lacking polypeptide binding to the chimeric antigen receptor is additionally administered to a subject, CAR can no longer target cancer cells, thereby restraining undue activity of CAR-T cells.

Advantageous Effects of Invention

The present disclosure provides an anti-HER2 affibody and a switch molecule comprising a cotinine-conjugated anti-HER2 affibody. When applied in combination with Cot-sCART, the cotinine-conjugated anti-HER2 affibody of the present disclosure reacts with HER2-positive cells to induce immune cell activity, thereby finding advantageous applications as switch molecules in sCART therapeutic agents.

DETAILED DESCRIPTION

Hereinafter, the present disclosure will be described in greater details with reference to the accompanying examples. However, these examples disclosed herein are only for illustrative purposes of the present disclosure, and it shall be obvious to a skilled person in the art that they should not be construed as limiting the scope of the present disclosure.

EXAMPLE

Unless stated otherwise, "%", used to indicate concentrations of particular substances, stands for (wt./wt.) % for solid/solid, (wt./vol.) % for solid/liquid, and (vol./vol.) % for liquid/liquid throughout the specification.

Example 1: Development of Affibody to HER2

Example 1-1. Selection of Affibody by Panning

Clones binding specifically to HER2 were selected from an affibody library by panning with HER2-ECD-Fc protein. In addition, the clones were analyzed for binding to HER2 expression cells. As a result, five affibodies were obtained.

For use in panning, the affibody library was rescued in a phage form by using VSCM13 helper phage. As many as or more than $10^{13}$ library phages were initially allowed to bind the antigen, with a total of four panning rounds conducted. In the strategy of selecting phages exhibiting higher affinity, the amount of the antigen was decreased (10 μg, 5 μg, 2 μg, and 1 μg) while the number of washes was increased (3, 5, 7, and 10 time) as the panning round was further repeated.

Figure 1:
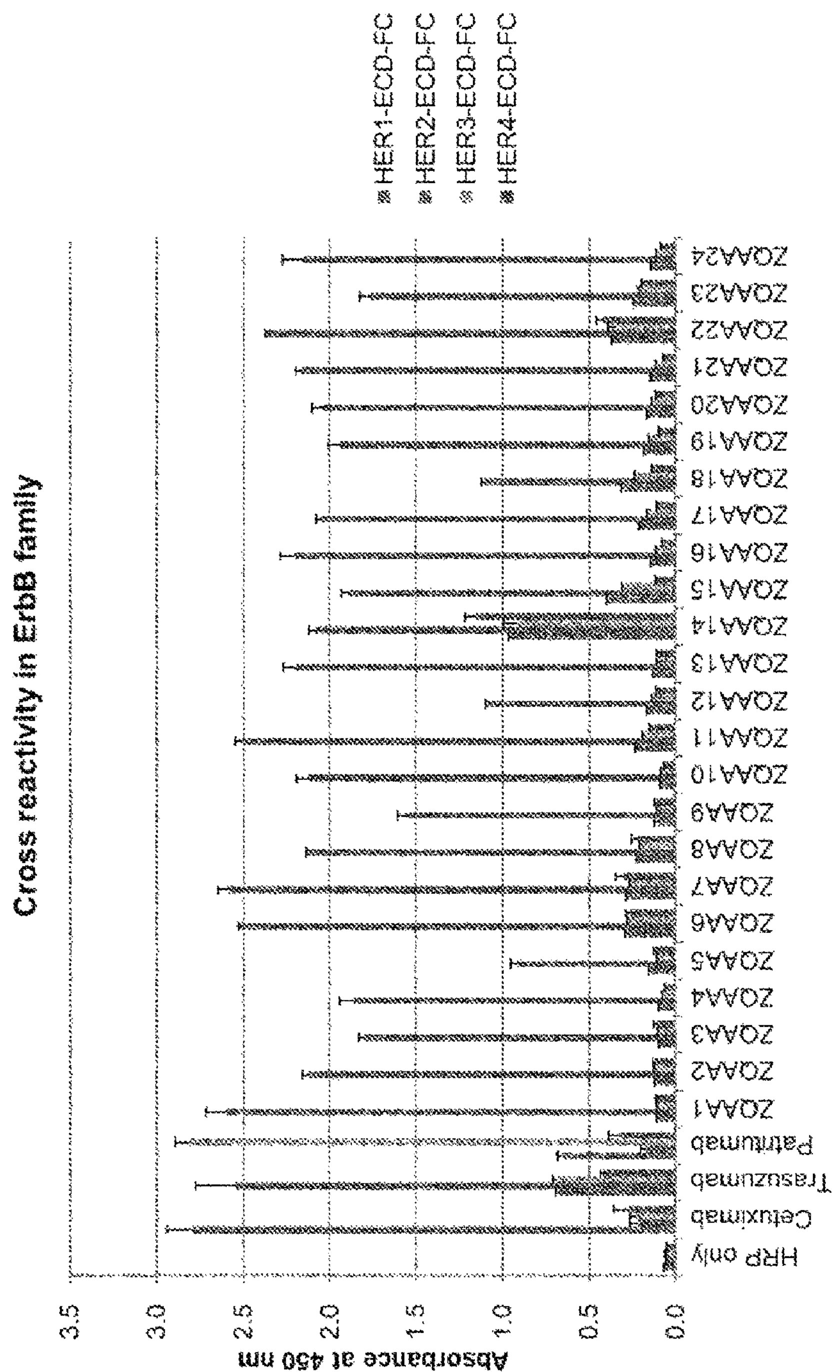
FIG. 1 is a graph showing affibodies specifically binding to HER2 in the form of periplasmic extracts.

Binder phages obtained in each panning round were analyzed for binding to the antigen. In this regard, ELISA was performed on the colonies resulting from infection into ER2537. In brief, a colony obtained by infecting binder phages was inoculated into an SB media (MOPS 10 g/L, Bacto YEAST extract 20 g/L, Trypton 30 g/L) and cultured until reaching an $OD_{600}$ of 0.8, followed by shaking incubation at 30° C. in the presence of 1 mM IPTG (LPS solution, IPTG025) to allow the overexpression of the affibody. Periplasmic extraction was performed using a BBS buffer (200 mM Boric acid, 150 mM NaCl, 1 mM EDTA). Binders were screened by ELISA using the extract. For ELISA, the affibody periplasmic extract was applied to a plate coated with 2 μg/mL of each of HER1-ECD-Fc, HER2-ECD-Fc, HER3-ECD-Fc, and HER4-ECD-Fc and treated with a secondary antibody (anti-HA-HRP (Roche, 12013819001)). After color development with TMB (BioFX, TMBC-1000-01), $OD_{450}$ values were read using an ELISA reader (PerkinElmer, Victor3) (FIG. 1). The ELISA data exhibited affibodies specifically binding to HER2 protein and 23 unique clones were identified by sequencing.

Figure 2A:
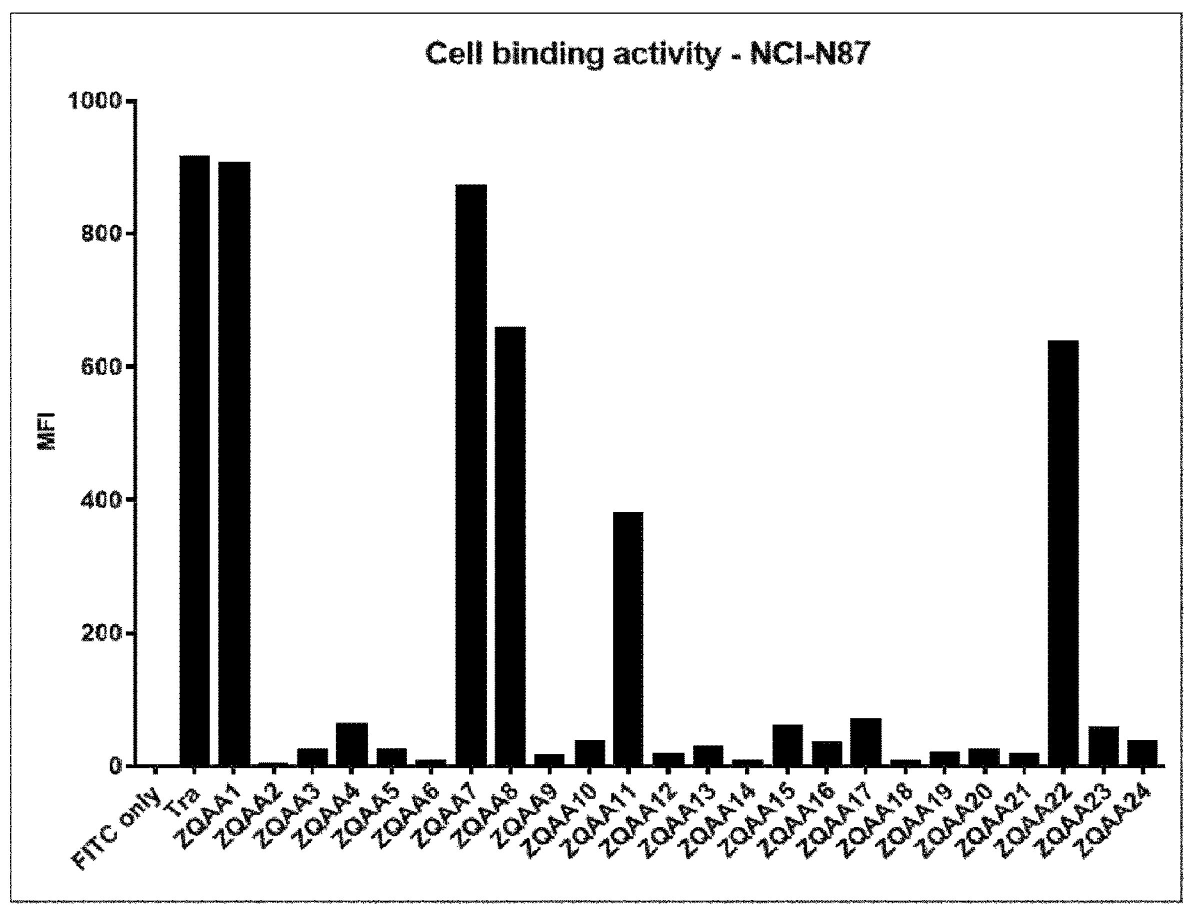
FIGS. 2*a*, 2*b* and 2*c* show graphs illustrating binding affinity of HER2-binding affibodies for three HER2-expressing cells in terms of MFI values (A. NCI-N87, B. SK-OV-3, C. MDA-MB-231).
Figure 2B:
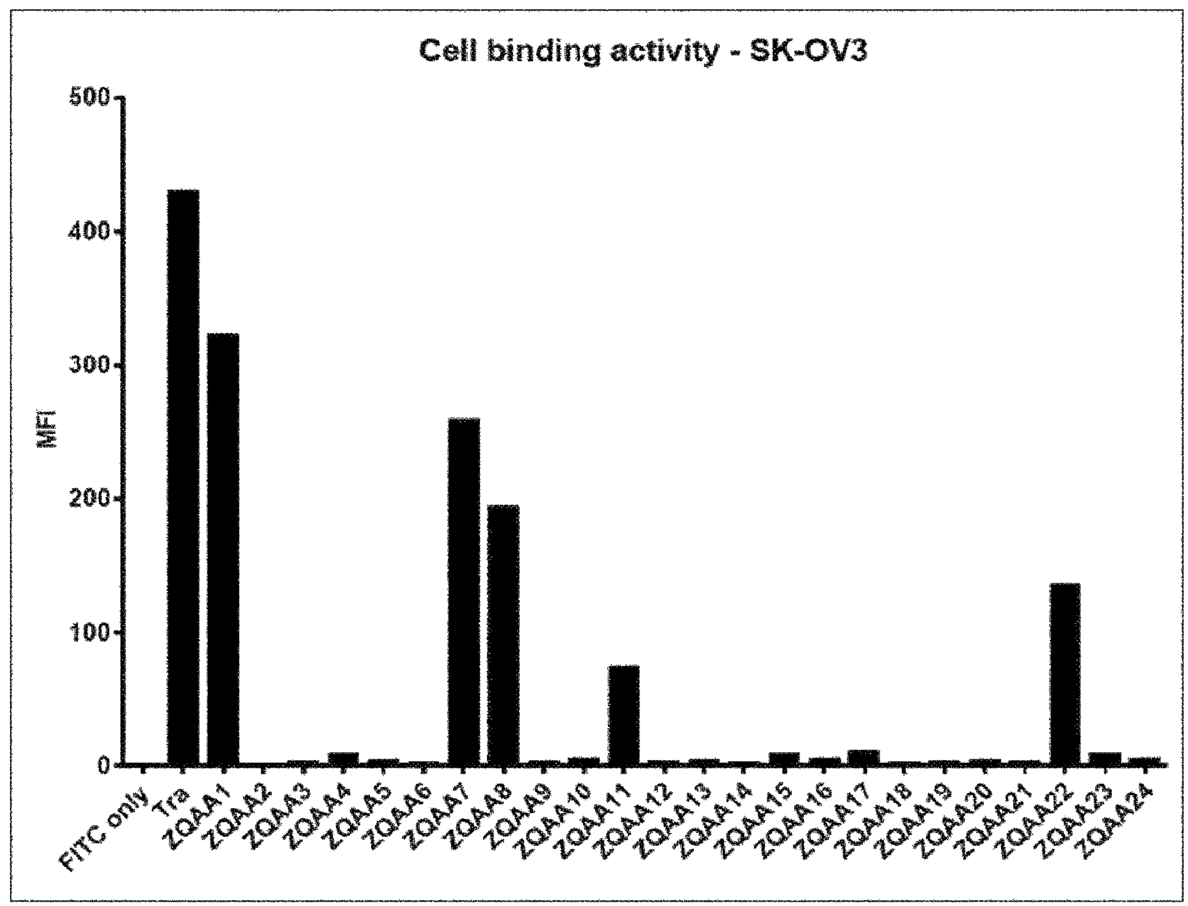
Figure 2C:
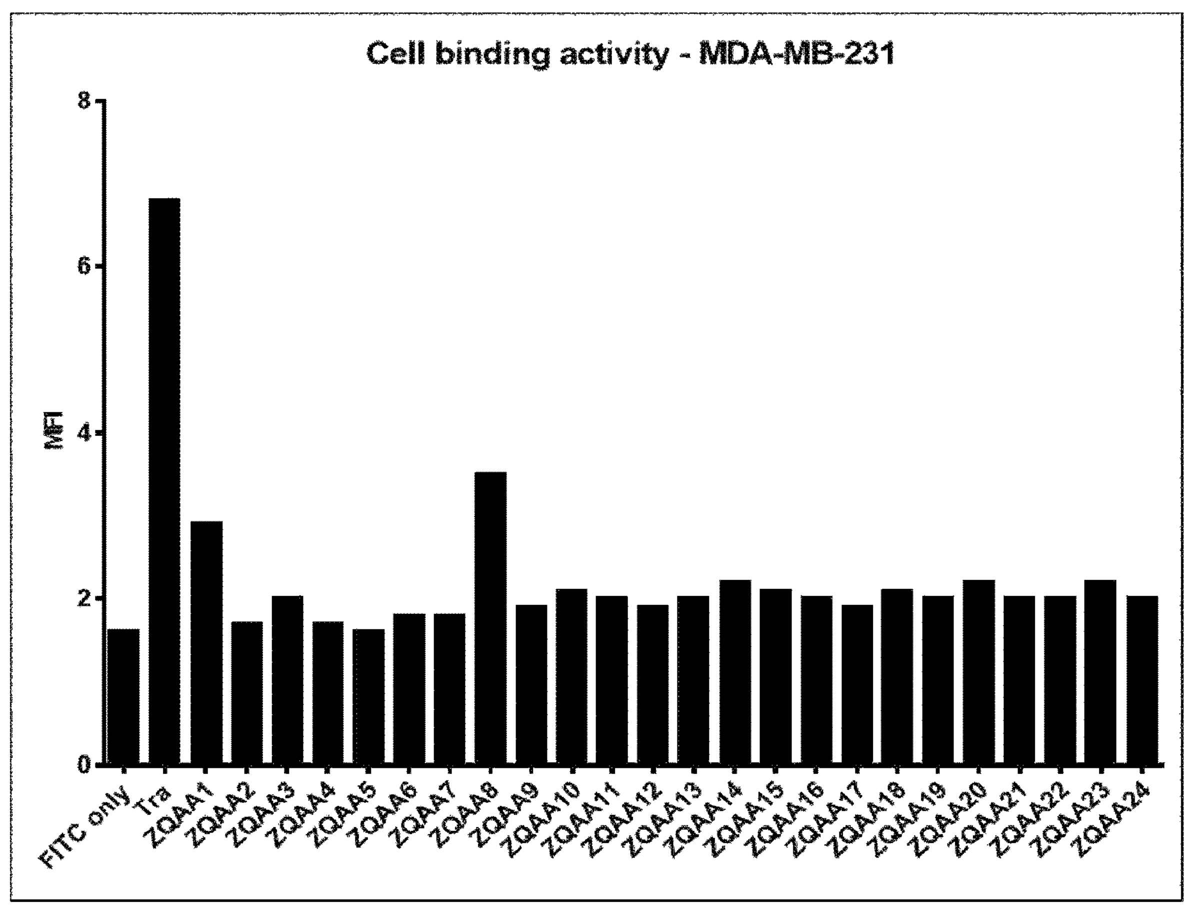

From the periplasmic extracts of the unique clones, cell binders were identified using the three HER2 expressing cell lines—NCI-N87 (ATCC, CRL-5822), SK-OV-3 (Korean Cell Line Bank, 30077), MDA-MB-231 (Korean Cell Line Bank, 30026). The three HER2 expressing cells were each prepared at a density of $5\times10^5$ cells/tube and centrifuged at 1200 rpm for 3 min to harvest cells. The cells were washed with PBS containing 5% FBS and then incubated with 200 μL of the affibody-containing periplasmic extract at 4° C. for 1 hour. The cells were washed three times through three rounds of centrifugation with 200 μL of 5% FBS-containing PBS at 1200 rpm for 3 min. Then, the cells were incubated with 1 μg/mL anti-HA-FITC (Life Technologies, A11013) at 4° C. for 45 min in a light-shielded condition. After being washed three times through three rounds of centrifugation with 200 μL of 5% FBS-containing PBS at 1200 rpm for 3 min, the cells were measured for fluorescence intensity by FACS (Beckmann coulter, FC500) (FIGS. 2*a* to 2*c*). Through the ELISA and cell binding test, five affibodies (ZQAA1, 7, 8, 11, 22) which had excellent binding affinity were selected (Table 1).

TABLE 1

| Name | Sequence | SEQ ID NO: |
|---|---|---|
| ZQAA1 | VDNKFNKELRVAYWEIVKLPNLNPYQSRAFIRSLYDDPS QSANLLAEAKKLNDAQAPK (SEQ ID NO: 1) | 1 |
| ZQAA7 | VDNKFNKELRGAYWEITSLPNLNHSQITAFIVSLYDDPSQ SANLLAEAKKLNDAQAPK (SEQ ID NO: 2) | 2 |
| ZQAA8 | VDNKFNKEMRDAYWEIVRLPNLNPPQSTAFIRSLYDDPS QSANLLAEAKKLNDAQAPK (SEQ ID NO: 3) | 3 |
| ZQAA11 | VDNKFNKEYMLAYWEIVKLPNLNYPQQHAFIRSLFDDPS QSANLLAEAKKLNDAQAPK (SEQ ID NO: 4) | 4 |
| ZQAA22 | VDNKFNKEINKAYWEIISLPNLNKEQHHAFIHSLYDDPSQ SANLLAEAKKLNDAQAPK (SEQ ID NO: 5) | 5 |

Example 1-2: Identification of Binding Affinity of Selected Affibody

Figure 3:
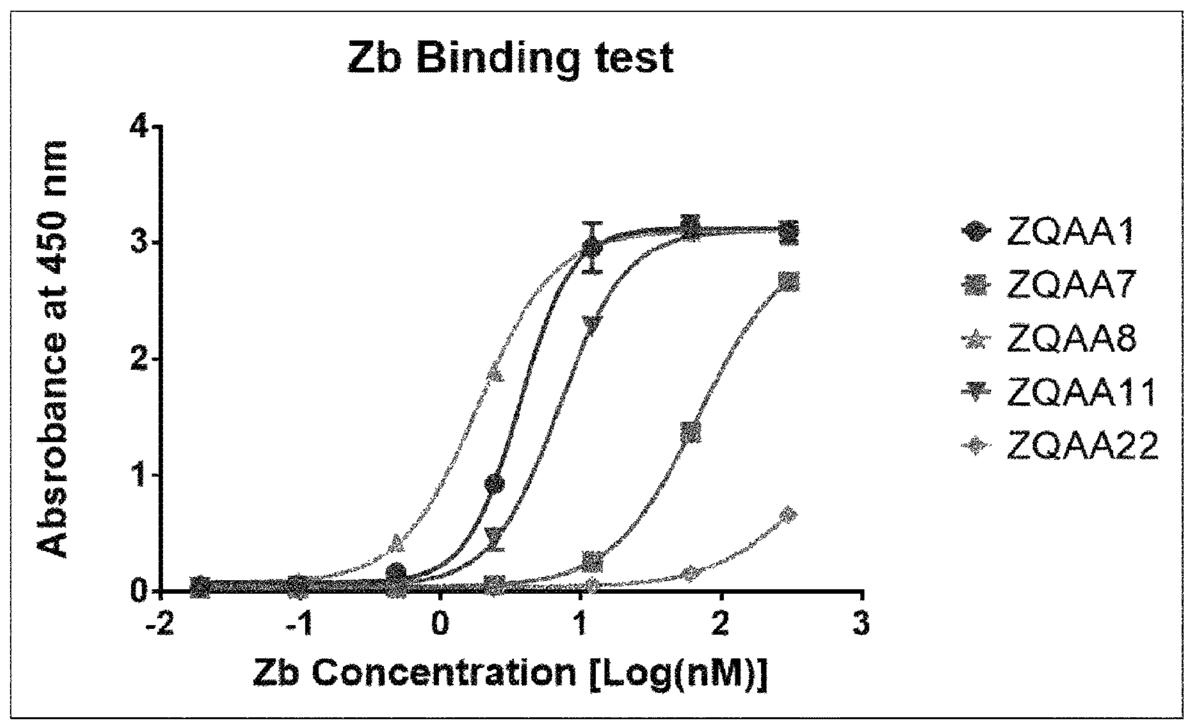
FIG. 3 is a graph quantitatively showing binding affinity of five Fc-coupled affibodies for HER2 protein.
Figure 4A:
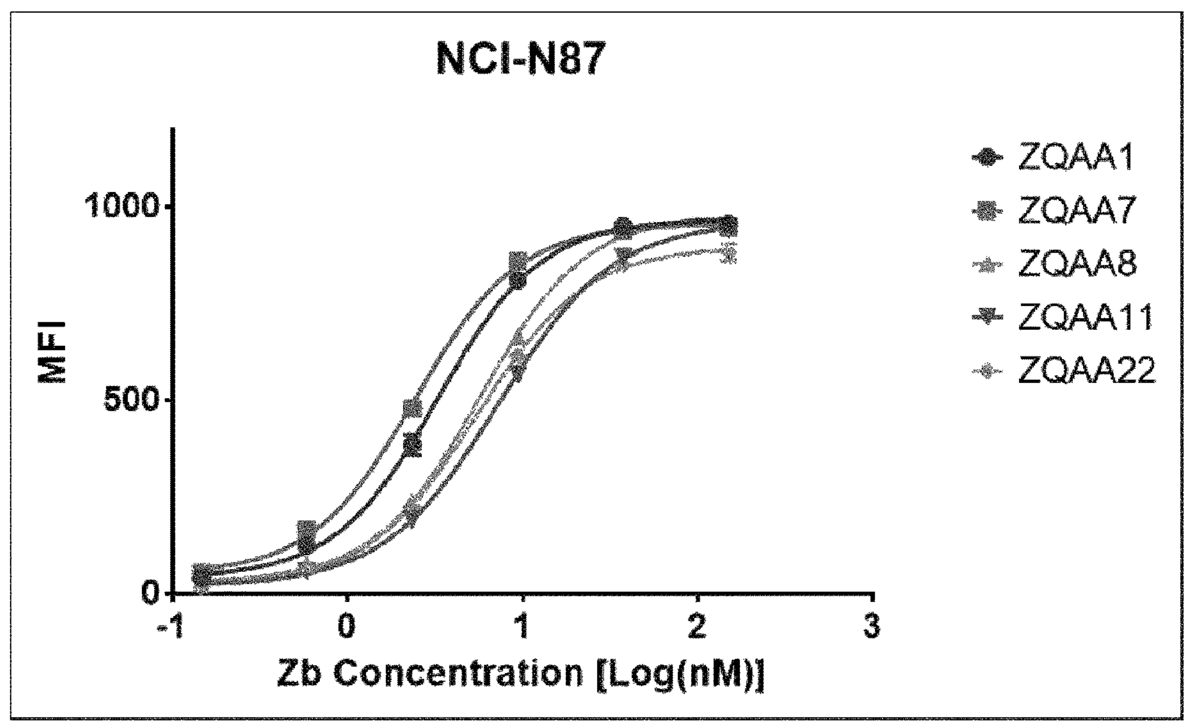
FIGS. 4*a*, 4*b*, 4*c* and 4*d* show graphs quantitatively analyzing the binding affinity of five Fc-coupled affibodies for four HER2-expressing cell lines (A. NCI-N87, B. SK-OV-3, C. MDA-MB-453, and D. MDA-MB-231).
Figure 4B:
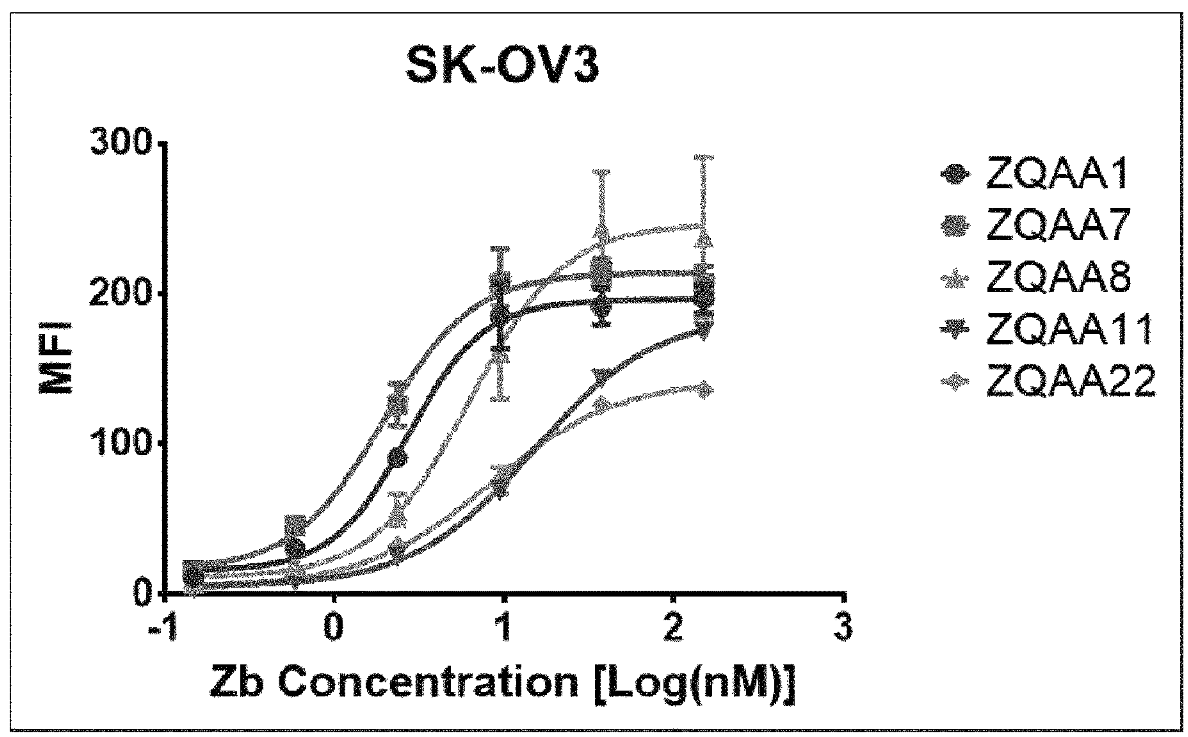
Figure 4C:
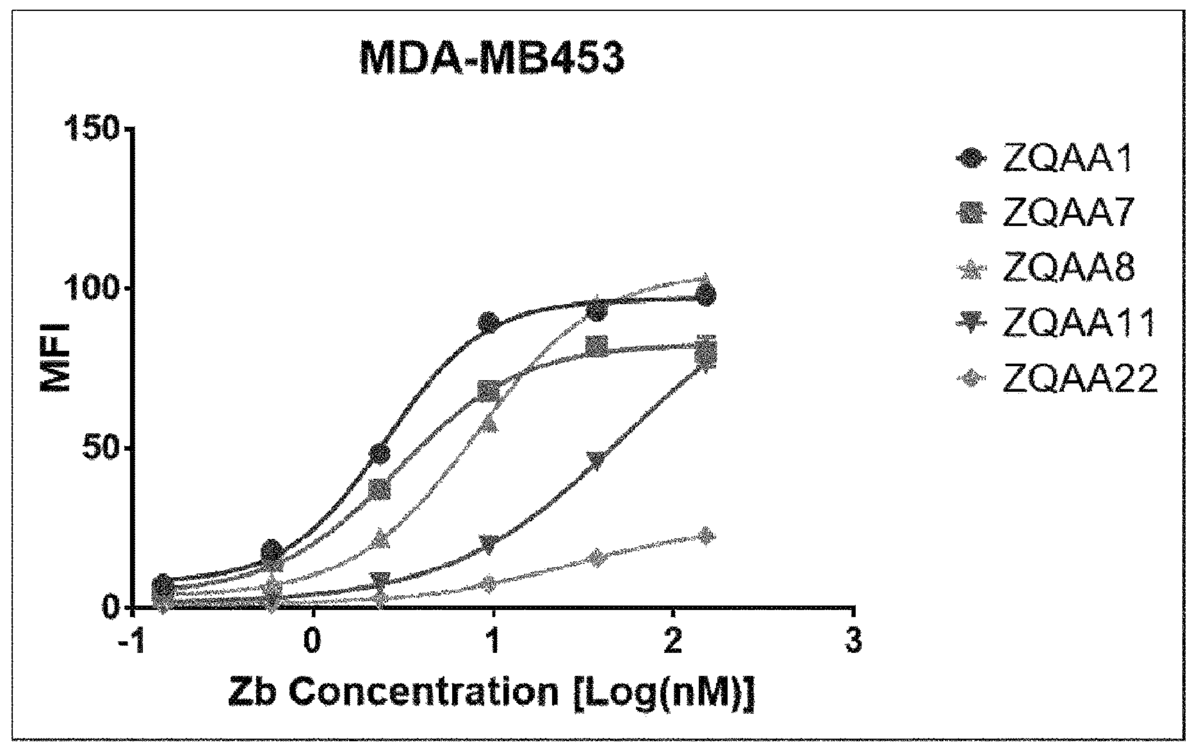
Figure 4D:
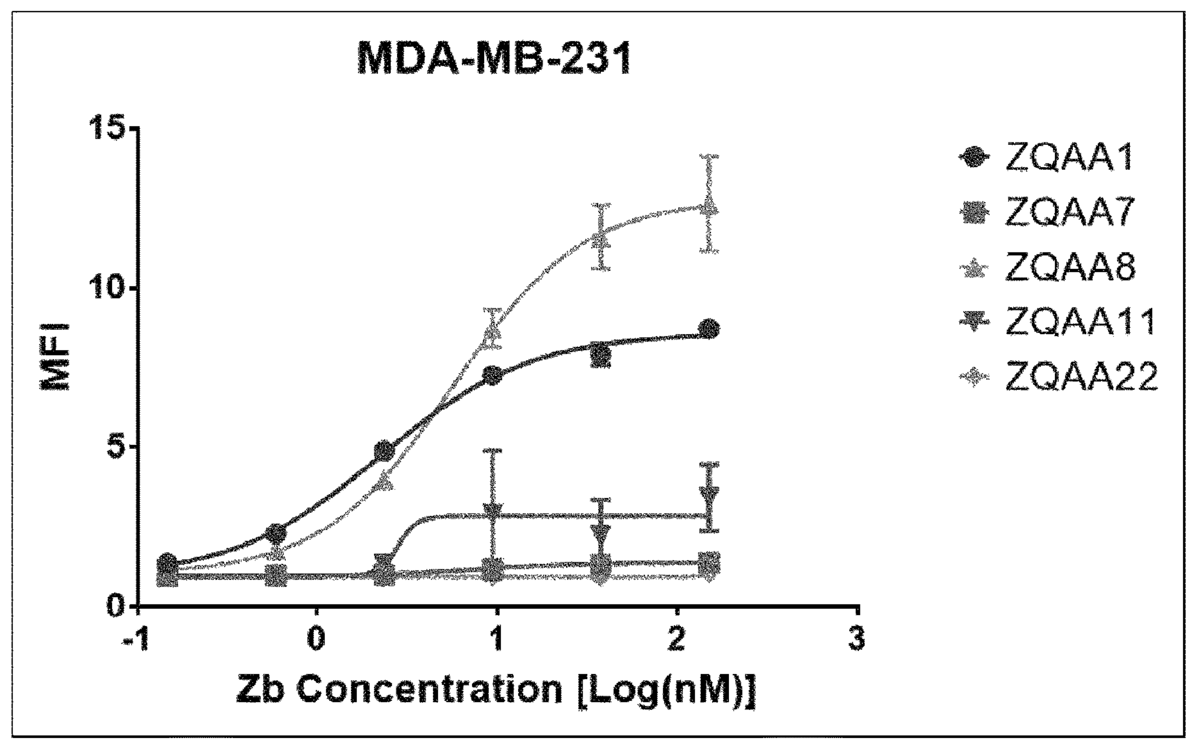

The five selected affibodies were cloned in an Fc-conjugated form (Zb-Fc) and analyzed for binding affinity for HER2 protein and HER2 expressing cells. For ELISA, the five purified Zb-Fc forms were ⅕ diluted for 7 points starting from 60 nM in a plate coated with 2 μg/mL hHER2-ECD-His. After treatment with a secondary antibody (anti-hIgG-Fc-HRP (Invitrogen, H10007)), a color was developed with TMB. $OD_{450}$ values were read using an ELISA reader, and $EC_{50}$ values were measured by means of Graph prism (FIG. 3, Table 2).

TABLE 2

| Affibody | ZQAA1 | ZQAA7 | ZQAA8 | ZQAA11 | ZQAA22 |
|---|---|---|---|---|---|
| $EC_{50}$ (nM) | 3.6 | 68.5 | 1.8 | 6.9 | N/D |

The affibodies were analyzed for binding affinity in HER2 expression cells. To this end, the four cell lines NCI-N87, SK-OV-3, MDA-MB-453 (Korean Cell Line Bank, 30131), and MDA-MB-231, which are in the descending order of HER2 expression, were each prepared at a density of $5\times10^5$ cells/tube. The cells were harvested by centrifugation at 1200 rpm for 3 min and washed with PBS containing 5% FBS. Thereafter, the five Zb-Fc forms were ⅕ diluted for 7 points starting from 60 nM and incubated at 4° C. for 1 hour.

The cells were washed three times by three rounds of centrifugation with 200 μL of 5% FBS-containing PBS at 1200 rpm for 3 min. Afterwards, the cells were incubated with 1 μg/mL anti-human-Fc-FITC (Life Technologies, A11013) at 4° C. for 45 min in a light-shielded condition. After being washed three times through three rounds of centrifugation with 200 μL of 5% FBS-containing PBS at 1200 rpm for 3 min, the cells were measured for fluorescence intensity by FACS. From the MFI measurements, $EC_{50}$ values were calculated using Graph prism (FIGS. 4*a* to 4*d*, Table 3).

TABLE 3

| $EC_{50}$ (nM) | ZQAA1 | ZQAA7 | ZQAA8 | ZQAA11 | ZQAA22 |
|---|---|---|---|---|---|
| NCI-N87 | 3.3 | 2.4 | 5.7 | 7.3 | 5.4 |
| SK-OV3 | 2.7 | 1.9 | 6.2 | 14.8 | 8.3 |
| MDA-MB-453 | 2.5 | 3.0 | 8.0 | 52.4 | 26.6 |
| MDA-MB-231 | 2.3 | 7.1 | 5.6 | N/D | N/D |

Example 2: Development of Cotinine-Conjugated Affibody and Identification of Activity Thereof Example 2-1: Construction of Cotinine-Conjugated Affibody Cotinine-conjugated affibody-cotinine complexes were synthesized such that the anti-HER2 affibodies of the present disclosure were used as switch molecules in an anti-switchable CAR system (Table 4).

TABLE 4

| Name | Sequence |
|---|---|
| Cot-ZQAA1-Cot | trans-4-Cotinine carboxylic acid-VDNKFNKELRVAYWEIVKLPNLNPYQSRAFIRSLYDDPSQSANLLAEAKKLNDAQAPK (SEQ ID NO: 1)-trans-4-Cotinine carboxylic acid |
| Cot-ZQAA7-Cot | trans-4-Cotinine carboxylic acid-VDNKFNKELRGAYWEITSLPNLNHSQITAFIVSLYDDPSQSANLLAEAKKLNDAQAPK (SEQ ID NO: 2)-trans-4-Cotinine carboxylic acid |
| Cot-ZQAA8-Cot | trans-4-Cotinine carboxylic acid-VDNKFNKEMRDAYWEIVRLPNLNPPQSTAFIRSLYDDPSQSANLLAEAKKLNDAQAPK (SEQ ID NO: 3)-trans-4-Cotinine carboxylic acid |
| Cot-ZQAA11-Cot | trans-4-Cotinine carboxylic acid-VDNKFNKEYMLAYWEIVKLPNLNYPQQHAFIRSLFDDPSQSANLLAEAKKLNDAQAPK(SEQ ID NO: 4)-trans-4-Cotinine carboxylic acid |
| Cot-ZQAA22-Cot | trans-4-Cotinine carboxylic acid-VDNKFNKEINKAYWEIISLPNLNKEQHHAFIHSLYDDPSQSANLLAEAKKLNDAQAPK(SEQ ID NO: 5)-trans-4-Cotinine carboxylic acid |

Example 2-2: Identification of Binding Affinity of Cotinine-Conjugated Affibody for HER2

Figure 5:
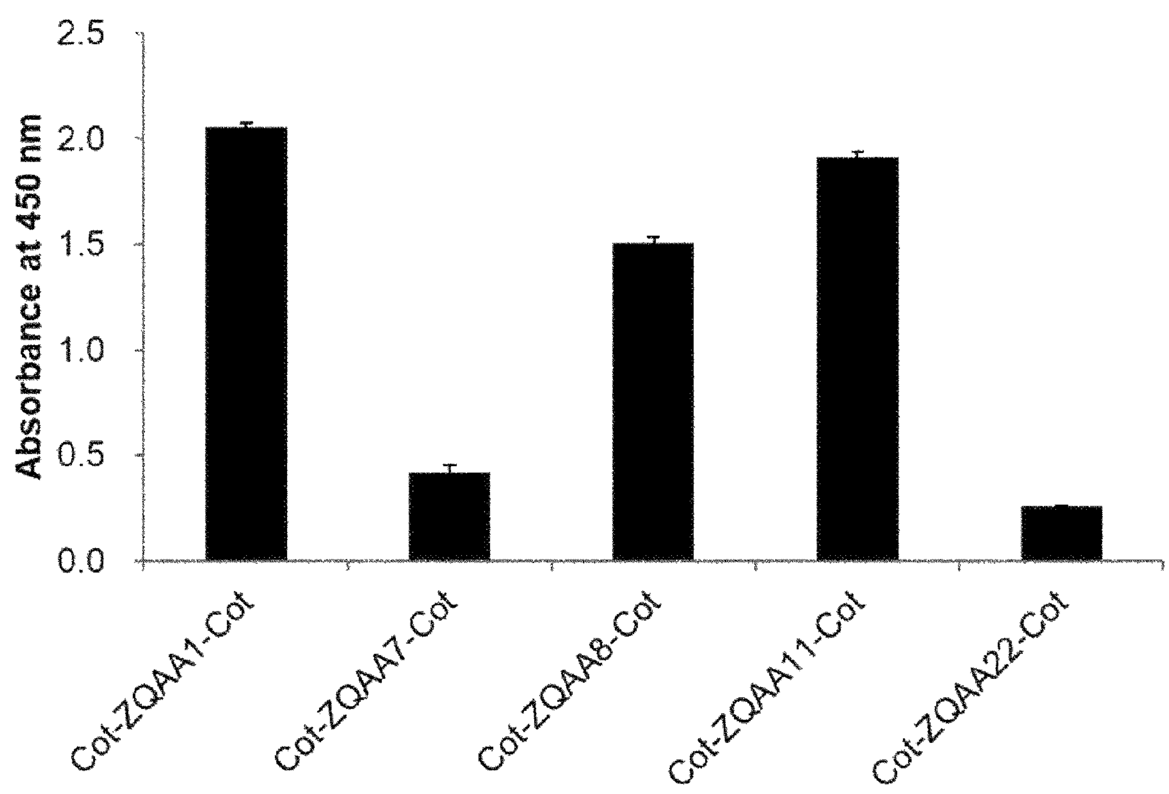
FIG. 5 is a graph quantitatively analyzing binding affinity of five cotinine-conjugated affibodies for HER2 protein.

The five cotinine-conjugated affibodies constructed in Example 2-1 were measured for binding affinity for HER2 protein. First, ELISA was carried out, with HER2-ECD-His protein serving as an antigen. The cotinine-conjugated affibodies were each applied at a density of 2 μg/mL to HER2-ECD-His protein-coated plates. A secondary antibody (Anti-Cotinine IgG) was applied to the HER-ECD-His/cotinine-conjugated affibody complex and labeled with a tertiary antibody (anti-hIgG-Fc-HRP (Invitrogen, H10007)). The labeled complex was quantitated by developing a color with TMB and reading $OD_{450}$ on an ELISA reader (PerkinElmer, Victor3) (FIG. 5).

Example 2-3. Construction of Lentivirus Containing Anti-Cotinine Antibody Fragment-Linked Chimeric Antigen Receptor A chimeric antigen receptor was developed using an anti-cotinine antibody fragment. After being subjected to codon optimization for a CD8 leader, a scFv-type anti-cotinine, a CD8 hinge and transmembrane region, a CD137 cytoplasmic region, and a CD3 zeta cytoplasmic region in the chimeric antigen receptor, the gene was cut with SpeI/XhoI and ligated to pLenti6-V5/DEST lentiviral vector (Invitrogen, V53306). The constructs thus obtained were identified by base sequencing. Amino acid and base sequences of the anti-cotinine antibodies and antigen-binding fragments thereof are represented in SEQ ID NOS: 9 to 18.

Each of the prepared lentiviral constructs was transduced, together with the plasmid pCMV-dR8.91 carrying the viral coat protein VSV-G (vesicular stomatitis Indiana virus G protein), gag, pol, and rev genes, into Lenti-X 293T cells (Takara Bio Inc., 632180). Transduction was performed using Lipofectamine 2000 (Invitrogen, 11668019) according to the manufacturer's protocol. After 72 hours, the cell culture containing lentivirus was 10-fold enriched by a centrifugal filter (Millipore, UFC910024) and stored.

Example 2-4. Preparation of Cytotoxic T Cell Presenting Anti-Cotinine Antibody-Bearing Chimeric Antigen Receptor on Surface (Cot-sCART)

Cytotoxic T cells on which anti-cotinine antibody fragment-bearing chimeric antigen receptors were presented were prepared using the lentivirus obtained in Example 2-3.

First, human naïve T cells were isolated and stimulated with Dynabeads™ Human T-Activator CD3/CD28 (Thermo Fisher Scientific, 11131D) for 24 hours. Thereafter, the lentivirus was transduced for 24 hours into the cells in the presence of polybrene (Sigma-Aldrich, H9268). Then, the medium was exchanged with a medium containing IL-2 (Gibco, CTP0021), followed by incubation at 37° C. in a 5% $CO_2$ atmosphere. T cells presenting the anti-cotinine antibody fragment-bearing chimeric antigen receptor on the surface thereof (Anti-Cotinine CAR-T cell, Cot-sCART) were used in experiments within 24 hours after preparation.

Example 2-5. Identification of Cytotoxic Effect by Using Cotinine-Conjugated Affibody and Cot-sCART The T cells Cot-sCART prepared in Example 2-4 and the cotinine-conjugated affibody complex were analyzed for introducing the activation of chimeric antigen receptor cells by recognizing HER2 on the cell surface.

Figure 6:
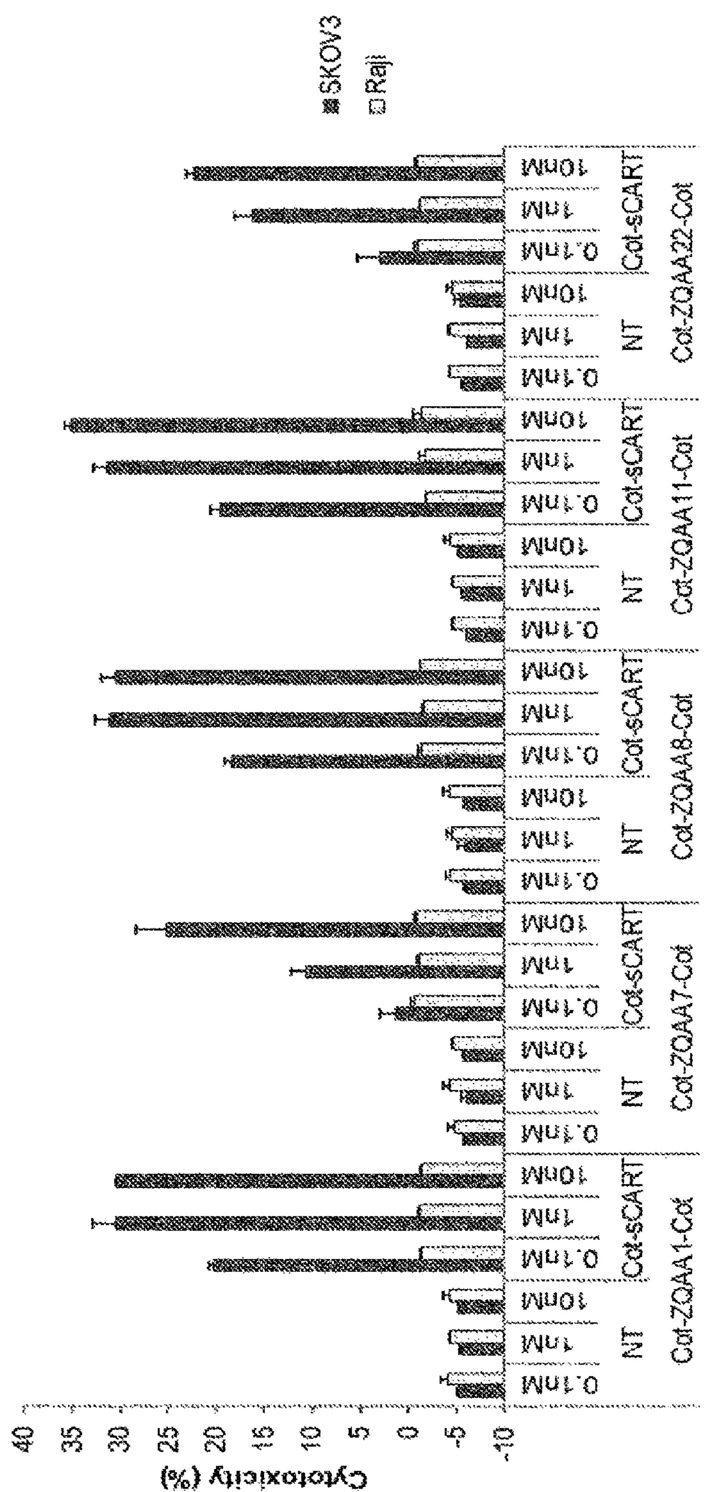
FIG. 6 is a graph showing cytotoxicity effects of cotinine-conjugated affibodies and chimeric antigen receptor T cells (Cot-sCART) using and anti-cotinine antibodies on HER2-positive SK-OV-3 cells and HER2-negative Raji cells.

Briefly, GFP-Luciferase-expressing lentivirus (Biosettia, GlowCell-16p-1) was introduced into the HER2-positive cell line SKOV-3 and the HER2-negative cell line Raji to establish SKOV3-Luc and Raji-Luc cell lines for use in experiments. First, SKOV3-Luc or Raji-Luc cells were seeded at a density of $1\times10^4$ cells/well into 96-well plates. The prepared cytotoxic T cells were added to the Luc cells-seeded plate at a suitable rate per well. The cotinine-conjugated affibody was added at predetermined concentrations (0.1, 1, and 10 nM) to the test group treated with the Luc cells and the cytotoxic T cells and incubated 37° C. for 24 hours in a 5% $CO_2$ atmosphere. Thereafter, cytotoxicity of the cytotoxic T cells was measured using a luciferase assay (Bio-Glo Luciferase assay system, Promega, G7941). For measurement of cytotoxic effects, the cytotoxic T cells, the cotinine-conjugated affibody, and the Luc cells were co-cultured after which the remaining SKOV3-Luc or Raji-Luc cells were lysed with 3× Lysis buffer (75 mM Tris (pH8.0), 30% glycerol, 3% Triton X100) to release a luciferase which was then reacted with a substrate. Relative lysis rates were given when the signal from the wells where only Luc cells had been cultured was set forth as 100%. As shown in FIG. 6, the cytotoxic effects were increased in a cotinine-conjugated affibody concentration-dependent manner. Relatively high cytotoxicity was observed in three cotinine-conjugated affibodies (Cot-ZQAA1-Cot, Cot-ZQAA8-Cot, and Cot-ZQAA11-Cot).

Example 2-6. Evaluation of Cotinine-Conjugated Affibody and Cot-sCART in Disease Animal Model The chimeric antigen receptor cells were assayed for activity in disease animal models using the T cell Cot-sCART prepared in Example 2-4 and the cotinine-conjugated affibody complex.

Figure 7A:
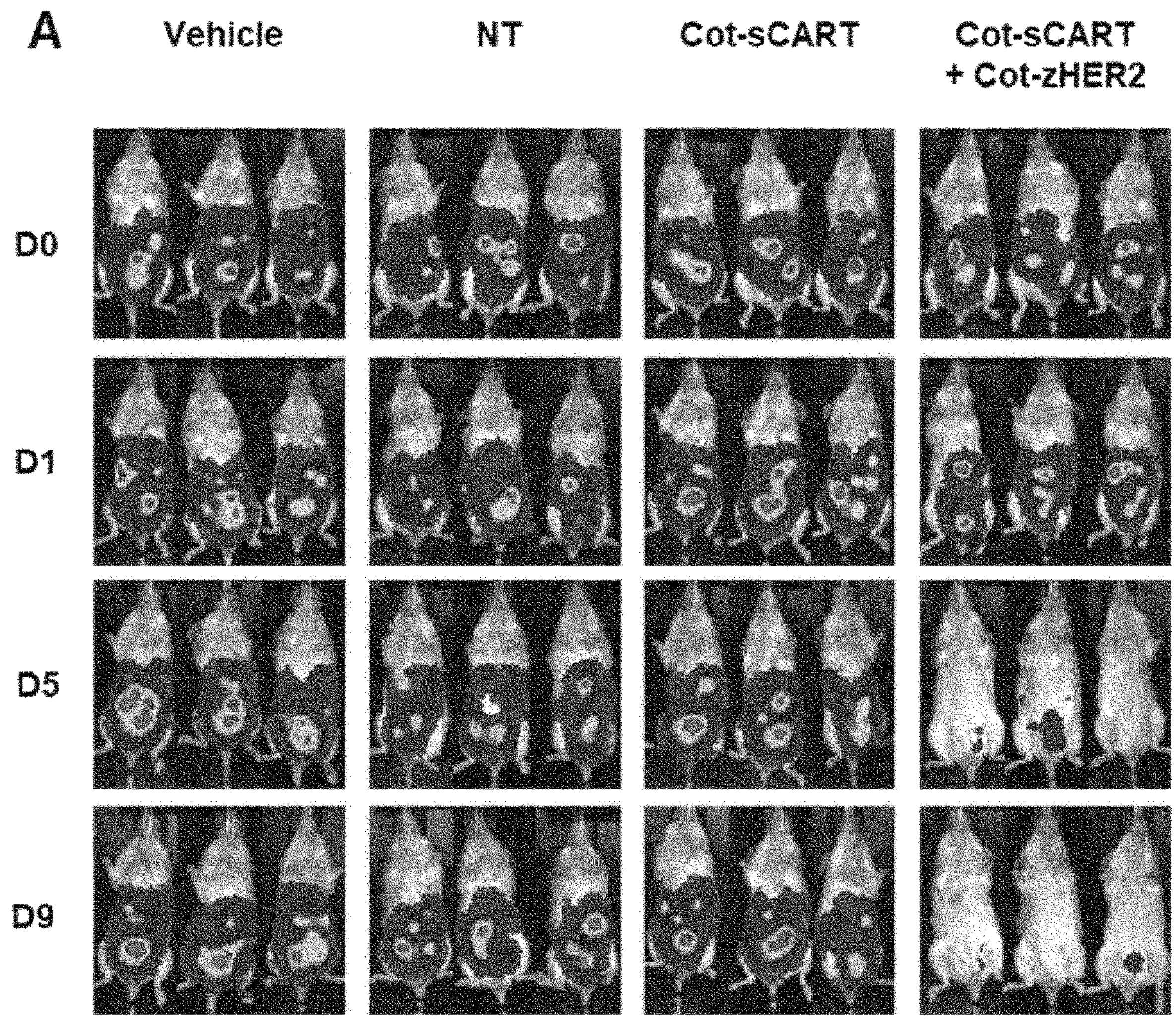
FIGS. 7*a* and 7*b* show effects of cotinine-conjugated affibodies and Cot-sCART on disease models constructed by applying SKOV3-Luc cells to immunodeficient mice (NSG) (A. Luminescence image, B. Luminescence signal quantitation data).
Figure 7B:
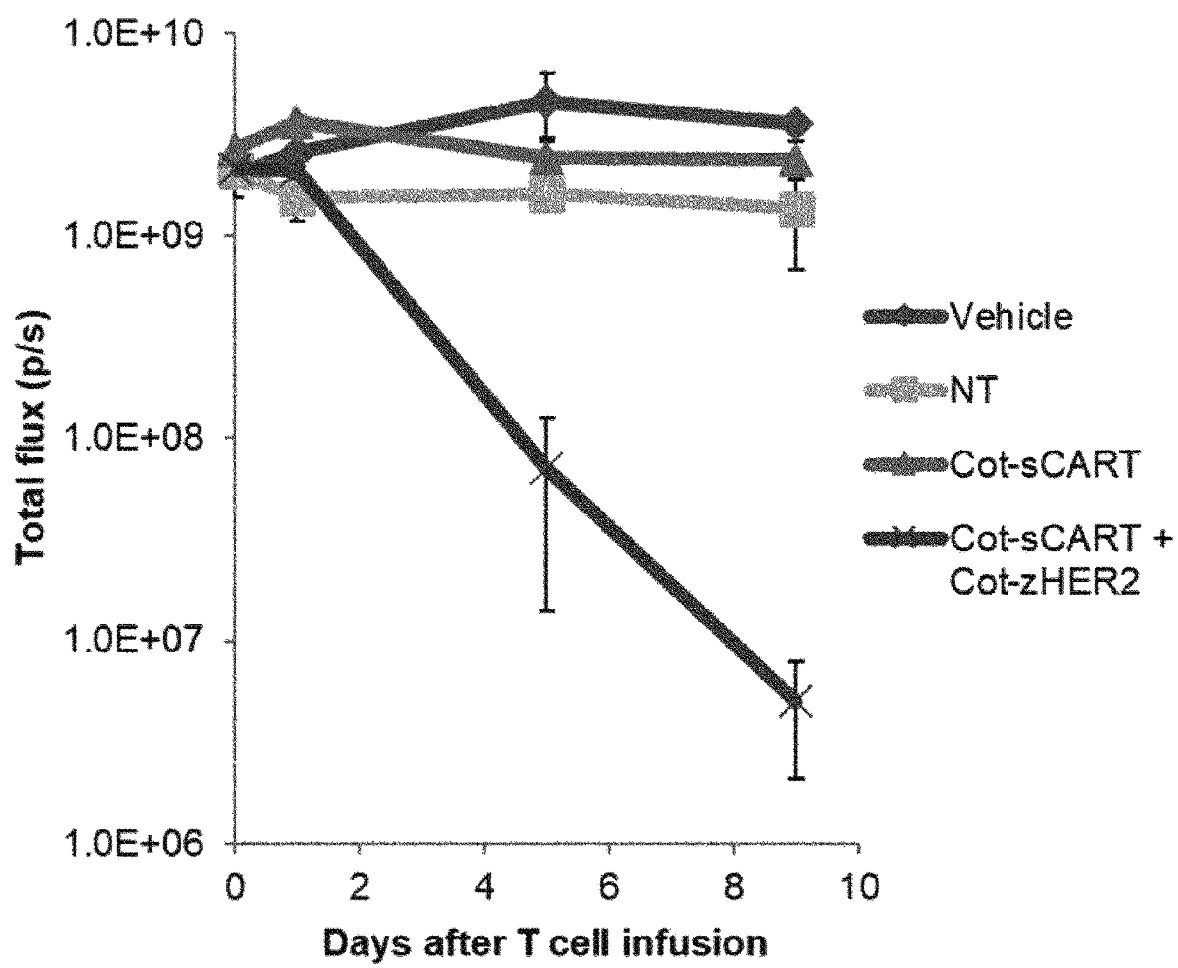

Briefly, the HER2-positive SKOV3-Luc cell line established in Example 2-5 were intraperitoneally injected into immunodeficient NSG mice (The Jackson Laboratory, 005557). On day 5 after injection, luciferin (Promega, P1043) was intraperitoneally injected. Then, the SKOV3-Luc cells formed in the abdomen were measured and randomly grouped using a luminescence spectrometer (PerkinElmer, IVIS 100). On day 7, Cot-sCART (2.0E+6 CART cells) were peritoneally injected, followed by the cotinine-conjugated affibody (Cot-zHER2; 0.25 mg/kg) every two days. After peritoneal injection of the cotinine-conjugated affibody, SKOV3-Luc cells were monitored using a luminescence spectrometer. As can be seen in FIGS. 7*a* and 7*b*, the number of SKOV3-Luc cells was observed to be decreased only in the NSG mice to which the Cot-sCART and the cotinine-conjugated affibody were administered.

Figure 8A:
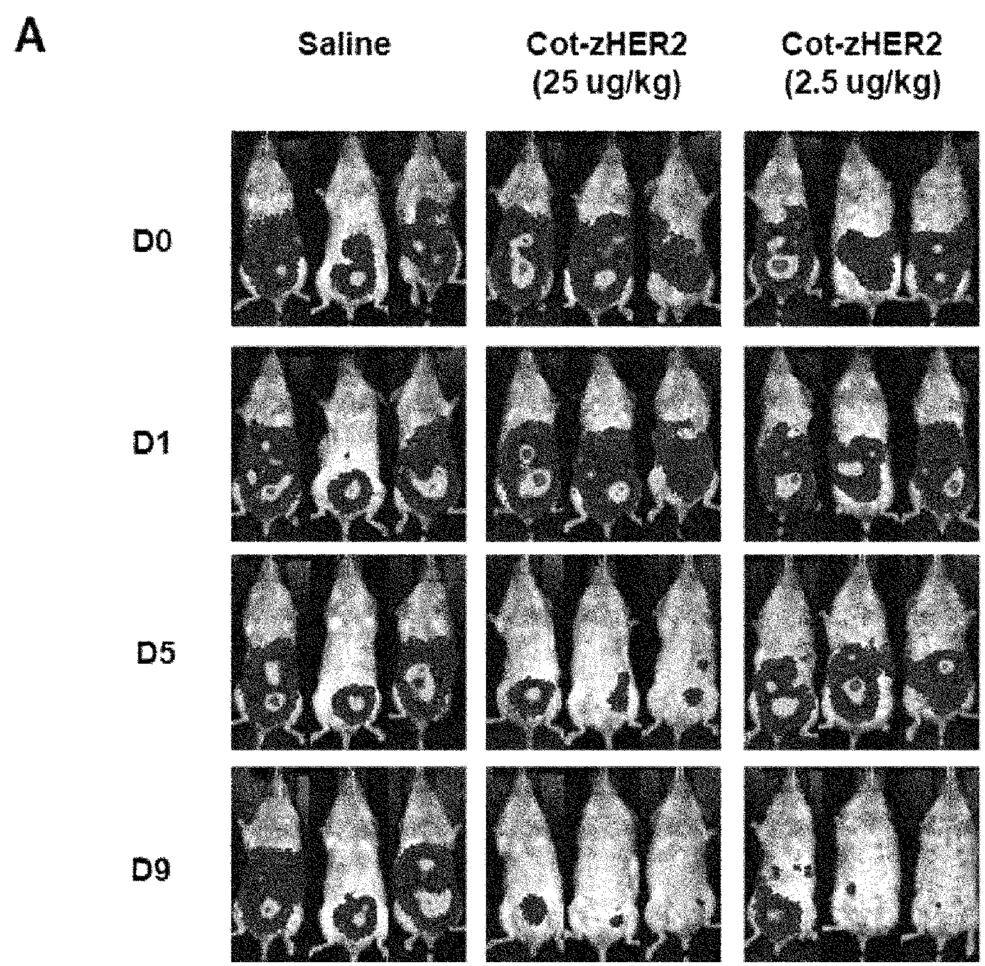
FIGS. 8*a* and 8*b* show effects of the cotinine-conjugated affibody and Cot-sCART on diseases constructed with SKOV3-Luc cells according to concentrations of the cotinine-conjugated affibody (A. Luminescence images, B. Luminescence signal quantitation data).
Figure 8B:
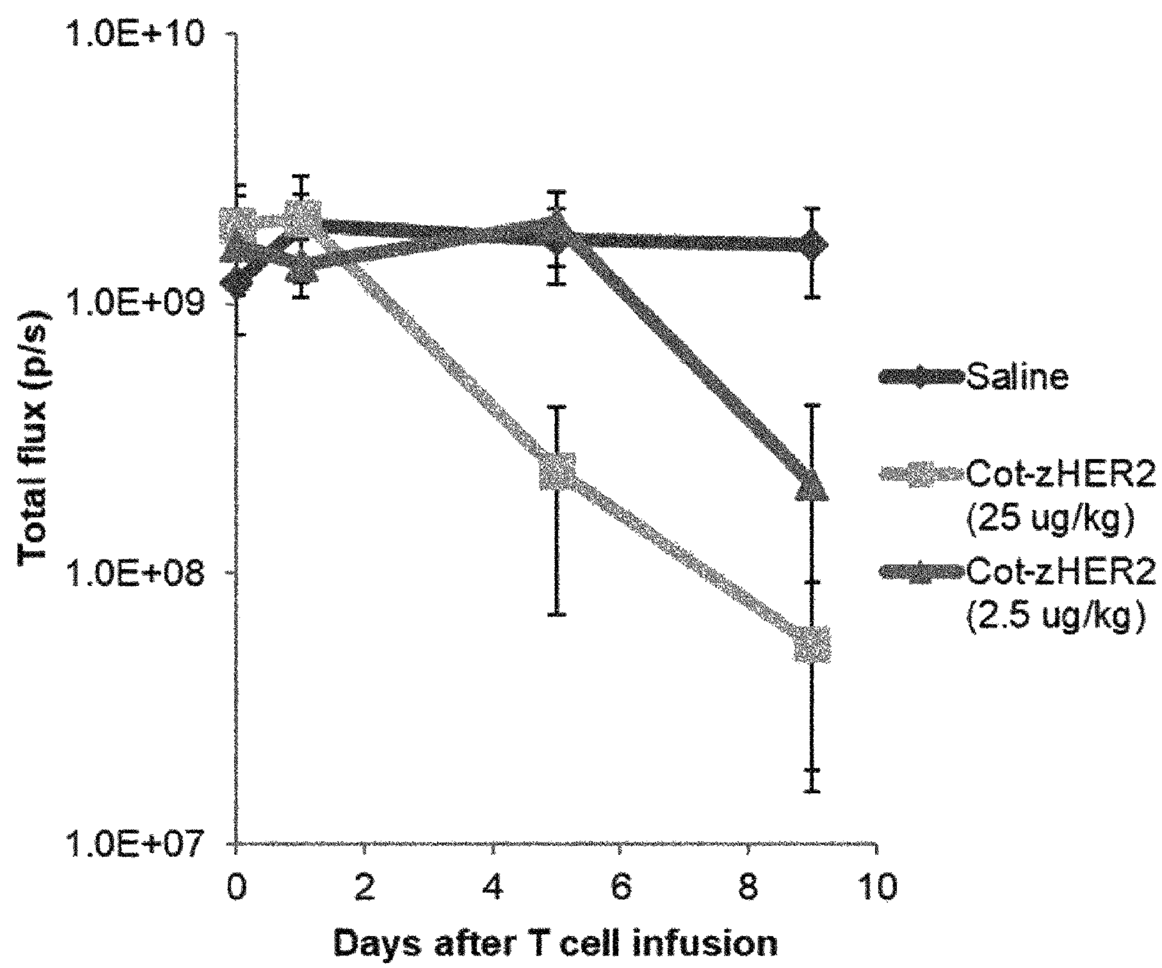

The activity of the chimeric antigen receptor cells was also monitored according to the concentration of the cotinine-conjugated affibody in disease animal models. Cot-sCART was peritoneally injected to the NSG mice where SKOV3-Luc cells had been established in the abdomen through the same peritoneal injection as in the aforementioned experiment. The NSG mice to which Cot-sCART was peritoneally injected were treated with 25 μg/kg and 2.5 μg/kg cotinine-conjugated affibody. As shown in FIGS. 8*a* and 8*b*, SKOV3-Luc cells were eliminated faster in the NSG mice to which the cotinine-conjugated affibody was injected at a higher dose.

Example 3: Affinity Maturation for ZQAA1 and ZQAA8

Example 3-1. Selection of Affinity-Improved Affibody Through Panning

Affinity maturation sub libraries of the affibodies ZQAA1 and ZQAA8 were constructed and selection was made of affibodies having improved affinity for HER2.

An affibody has a structure including three helices among which Helix1 and Helix2 are involved in binding a target and have variations on a total of 13 amino acid residues. For ZQAA1 and ZQAA8, sub-libraries in which random variations were given to 7 amino acid residues on Helix1 and 6 amino acid residues on Helix2 were constructed, respectively. Each sub-library was rescued in phage forms with VSCM13 helper phage before use in panning. As many as or more than $10^{13}$ library phages were initially applied to the antigen. Biotin-HER2-ECD-Fc was linked via Dynabeads M-280 streptavidin (Invitrogen, 11205D), followed by 5 rounds of panning in which the rescued phages were bound. In the strategy of selecting phages exhibiting higher affinity, the amount of the antigen was decreased (100 nm, 10 nM, 1 nM, 0.1 nM, and 0.01 nM) while the number of washes was increased (10, 15, 20, 25, and 30 times) as the panning round was further repeated. The binder phages obtained in each round of panning were analyzed for binding to the antibody as measured by ELISA for colonies resulting from infection into ER2537. Base sequencing identified 10 unique clones in the helix1 sub-library of ZQAA1, 23 unique clones in the helix2 sub-library of ZQAA1, 0 unique clones in the helix1 sub-library of ZQAA8, and 35 unique clones in the helix2 sub-library of ZQAA8.

Using periplasmic extracts of the unique clones, the two methods of extended wash and comparison of binding relative to expression were conducted to make selection against parental clones. Colonies resulting from infection of binder phages were inoculated into SB media (MOPS 10 g/L, Bacto YEAST extract 20 g/L, Trypton 30 g/L) and cultured until reaching an $OD_{600}$ of 0.8, followed by shaking incubation at 30° C. in the presence of 1 mM IPTG (LPS solution, IPTG025) to allow the overexpression of the affibody. Periplasmic extraction of the affibodies was performed using a BBS buffer (200 mM Boric acid, 150 mM NaCl, 1 mM EDTA).

In the extended wash method, the affibody periplasmic extract was applied to the plate coated with 2 μg/mL HER2-ECD-Fc and then treated with a secondary antibody (anti-HA-HRP (Roche, 12013819001)). After color development with TMB (BioFX, TMBC-1000-01), $OD_{450}$ values were read using an ELISA reader (PerkinElmer, Victor3). Simultaneously, the affibody periplasmic extracts were applied to the HER2-ECD-Fc-coated plates and stood in a wash buffer (0.05% Tween in PBS) for 2 hours, followed by treatment with a secondary antibody (anti-HA-HRP (Roche, 12013819001)). Color development with TMB (BioFX, TMBC-1000-01) was carried out before measurement of $OD_{450}$ values by an ELISA reader (PerkinElmer, Victor3). Comparison of O.D. values was made between the plates that had stood and not stood in the wash buffer so as to select improved clones relative to parental clones.

In the method of comparing binding affinity relative to expression, a serial dilution of the affibody periplasmic extract from the original solution was applied to the plates coated with 2 μg/mL HER2-ECD-Fc and then treated with a secondary antibody (anti-HA-HRP (Roche, 12013819001)). After color development with TMB (BioFX, TMBC-1000-01), $OD_{450}$ values were read on an ELISA reader (PerkinElmer, Victor3). In addition, a serial dilution of the periplasmic extract from the original solution was dotted to NC membranes. After the extracts were adsorbed and dried thereon, the NC membranes were incubated for 1 hour in 5% BSA in TBST. Thereafter, the membranes were treated with anti-HA-HRP (Roche, 12013819001) and then subjected to color development in an EDC solution (AbClon, Abc-3001). Expression levels were measured using an imaging system (Bio-rad, ChemiDoc touch). Selection was made of clones which exhibited ELISA $OD_{450}$ values superior to the parental values at diluted concentrations at which expression levels were not detected. Five clones were selected for ZQAA1 and one clone for ZQAA8. Cloning was conducted in Zb-Fc forms.

Figure 9A:
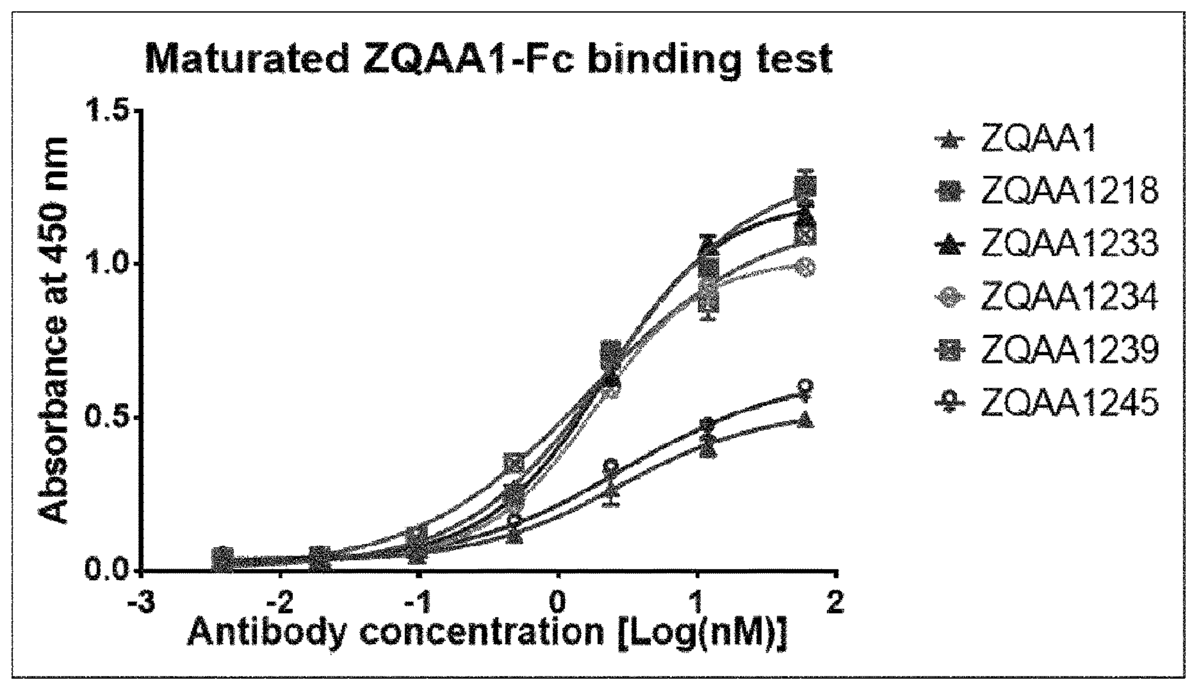
FIGS. 9*a* and 9*b* show quantitative comparisons of binding affinity of the affinity-improved clones produced in the Fc-coupled form for HER2 protein.
Figure 9B:
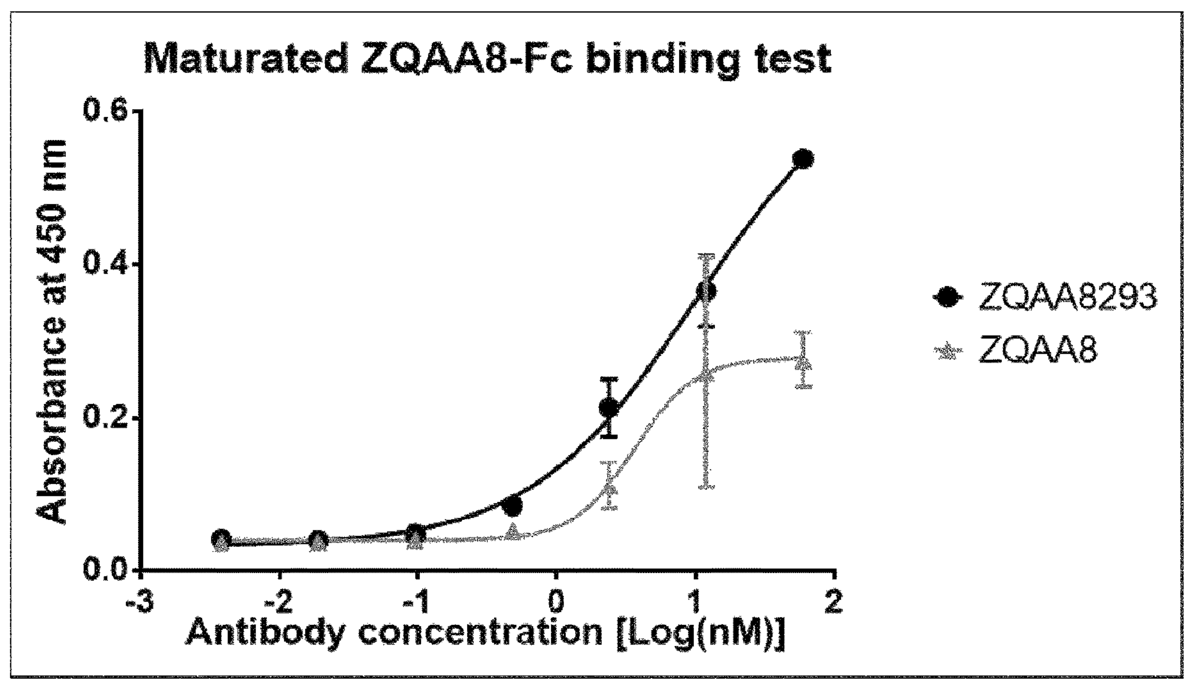

Using ELISA and BLI methods, each of the Zb-Fc proteins produced in animal cells was measured for KD for HER2 protein in comparison with parental clones. For ELISA, the purified Zb-Fc proteins were each ⅕ diluted for 7 points starting from 60 nM before application to plates coated with 2 μg/mL hHER2-ECD-his protein. Treatment with a secondary antibody (anti-hIgG-Fc-HRP (Invitrogen, H10007)) was followed by color development with TMB (BioFX, TMBC-1000-01). $OD_{450}$ values were measured using an ELISA reader (PerkinElmer, Victor3) (FIGS. 9*a* and 9*b*).

Some of the clones selected through ELISA were measured for KD values by a BLI method. Zb-Fc proteins were immobilized at a concentration of 2-5 μg/mL suitable for each clone to the AR2G sensor chips (PALL, 18-5092) by an amine coupling method using EDC/NHS. In order to measure KD values, ranging from 800 nM to 12.5 nM to the Zb-Fc-immobilized sensor chips, hHER2-ECD-his protein was allowed to bind at concentrations suitable for each clone for 10 min and then was dissociated for 15 min. As a result, clones which have KD values about 11-fold higher than those of the parental clones were acquired (Table 5). On the basis of the measurements, selection was made of ZQAA1234, ZQAA1239, and ZQAA8293 as affibodies optimized for HER2.

TABLE 5

| Name | Full $R^2$ | kon(1/Ms) | kdis(1/s) | KD(M) |
|---|---|---|---|---|
| ZQAA1 | 0.98 | 2.5E+04 | 7.4E−03 | 2.9E−07 |
| ZQAA1218 | 0.99 | 2.1E+04 | 3.1E−03 | 1.5E−07 |
| ZQAA1233 | 0.99 | 2.4E+04 | 1.5E−03 | 6.5E−08 |
| ZQAA1234 | 0.99 | 5.5E+04 | 1.4E−03 | 2.6E−08 |
| ZQAA1239 | 0.98 | 3.3E+04 | 1.6E−03 | 4.9E−08 |
| ZQAA1245 | 0.99 | 4.2E+04 | 5.5E−03 | 1.3E−07 |
| ZQAA8 | 0.99 | 2.0E+04 | 5.0E−03 | 2.5E−07 |
| ZQAA8293 | 0.99 | 4.0E+04 | 4.5E−03 | 1.1E−07 |

Example 4: Switch Production and Activity Analysis of Optimized Affibody to HER2

Example 4-1. Preparation of Cotinine-Conjugated Affibody

For use as a switch molecule in an anti-switchable CAR system, the optimized anti-HER2 affibody according to the present disclosure was synthesized into an antibody-cotinine complex (Switch molecule) through cotinine conjugation (Table 6).

TABLE 6

| Name | Sequence |
|---|---|
| Cot-ZQAA1234 | trans-4-Cotinine carboxylic acid-VDNKFNKELRVAYWEIVKLPNLNPPQITAFIRSLYDDPSQSANLLAEAKKLNDAQAPK (SEQ ID NO: 6) |
| Cot-ZQAA1239 | trans-4-Cotinine carboxylic acid-VDNKFNKELRVAYWEIVKLPNLNPKQITAFIKQLYDDPSQSANLLAEAKKLNDAQAPK (SEQ ID NO: 7) |
| Cot-ZQAA8293 | trans-4-Cotinine carboxylic acid-VDNKFNKEMRDAYWEIVRLPNLNRIQSVAFIRQLYDDPSQSANLLAEAKKLNDAQAPK (SEQ ID NO: 8) |

Example 4-2. Binding Affinity of Cotinine-Conjugated, Optimized Affibody for HER2

The three cotinine-conjugated, optimized affibodies prepared in Example 4-1 were analyzed for binding affinity for HER2.ECD. The binding affinity of the cotinine-conjugated, optimized affibodies for HER2.ECD was measured using ELISA in the same manner as in Example 2-2 (FIG. 10).

In addition, binding affinity for the HER2-positive cell line SKOV-3 was also measured. The cotinine-conjugated, optimized affibodies were labeled in the same manner as in Example 2-3 and the antibody fragments binding to the cell line were analyzed by flowcytometry (FIG. 11).

Figure 10:
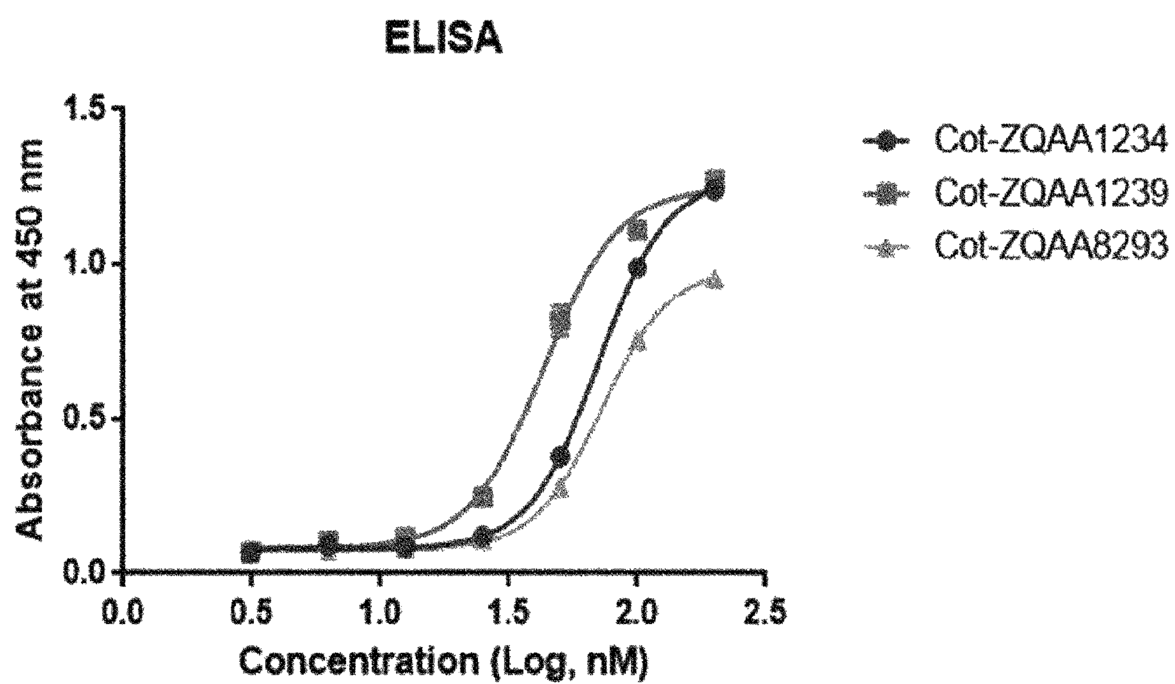
FIG. 10 is a graph showing quantitative analysis of the binding affinity of the cotinine-conjugated, optimized affibodies for HER2 protein.
Figure 11:
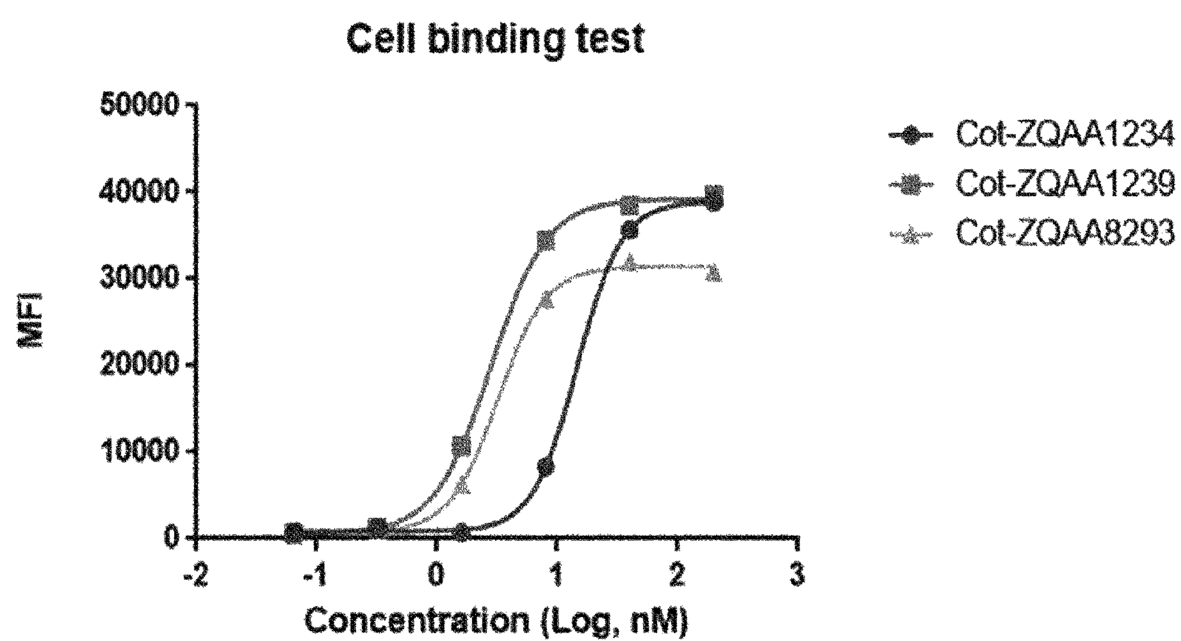
FIG. 11 is a graph showing binding affinity of the cotinine-conjugated, optimized affibodies for the HER2-expressing cell line SK-OV-3.

As can be seen in FIGS. 10 and 11, the three cotinine-conjugated, optimized affibodies (Cot-ZQAA1234, Cot-ZQAA1239, and Cot-ZQAA8293) were measured for binding affinity.

Figure 12:
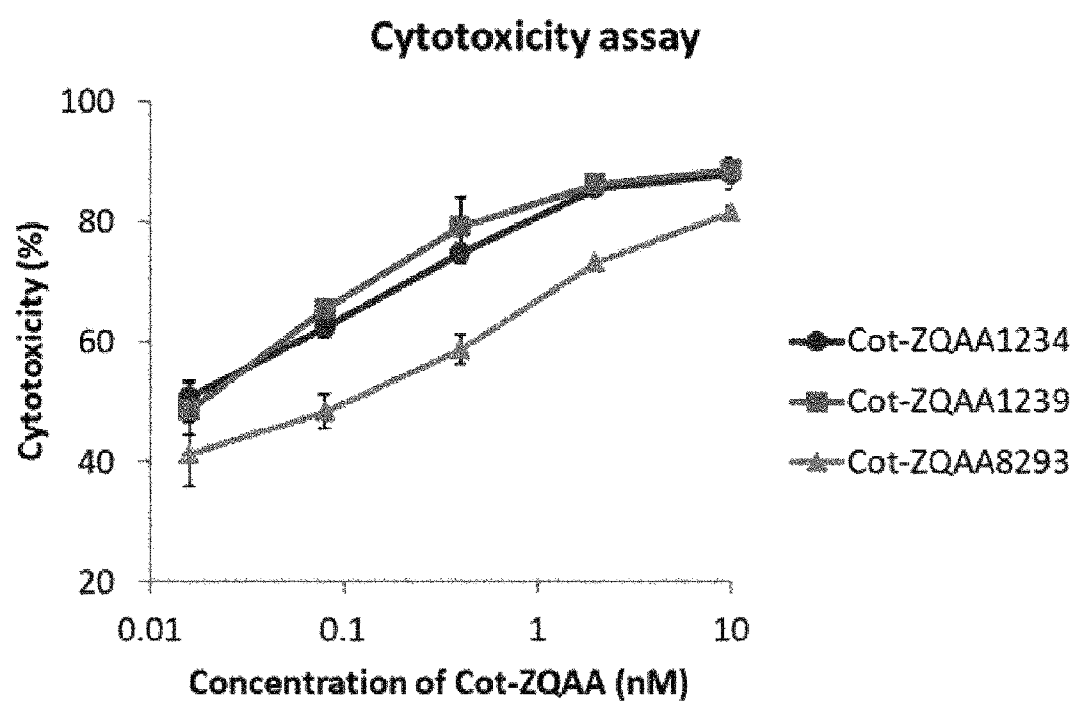
FIG. 12 is a graph showing cytotoxic effects of the cotinine-conjugated, optimized affibody and the Cot-sCART on the HER2 positive cell line SK-OV-3.

Example 4-3. Cytotoxic Effect of Cotinine-Conjugated, Optimized Affibody and Cot-sCART The Cot-sCART prepared in Example 2-4 and the cotinine-conjugated, optimized affibody were analyzed for cytotoxicity. In this regard, an analysis was made to examine whether the T cell/cotinine-conjugated affibody complex could recognize HER2 on the cell surface to induce the activation of the chimeric antigen receptor cells. SKOV3-Luc or Raji-Luc cells were co-cultured with Cot-sCART in the presence of the cotinine-conjugated, optimized affibody in the same manner as in Example 2-5, after which the cytotoxic T cells were measured by a luciferase assay (Bio-Glo Luciferase assay system, Promega, G7941). As shown in FIG. 12, the cytotoxicity increased with the concentration of the cotinine-conjugated, optimized affibodies treated. Among the three cotinine-conjugated, optimized affibodies (Cot-ZQAA1234, Cot-ZQAA1239, and Cot-ZQAA8293), relatively high cytotoxicity was observed in Cot-ZQAA1234 and Cot-ZQAA1239.

This application contains references to amino acid sequences and/or nucleic acid sequences which have been submitted herewith as the sequence listing text file entitled "000259usnp_SequenceLisiting_revised_ST25.txt", file size 15,480 Bytes (B), created on 12 Dec. 2024. The aforementioned sequence listing is hereby incorporated by reference in its entirety pursuant to 37 C.F.R. § 1.52(e).

What is claimed is:

1. An anti-HER2 Z-domain polypeptide, comprising the amino acid sequence of any one of SEQ ID NOs: 1 to 8.

2. A switch molecule for activating chimeric antigen receptor-effector cells, the switch molecule comprising a cotinine-conjugated anti-HER2 Z-domain polypeptide, wherein the anti-HER2 Z-domain polypeptide comprises the sequence as set forth in any of SEQ ID NOs: 1-8.

3. The switch molecule of claim 2, wherein the activation of the effector cell results in cytotoxicity against a target cell, cytokine secretion, or a combination thereof.

4. The switch molecule of claim 2, wherein the effector cell is selected from the group consisting of a dendritic cell, a killer dendritic cell, a mast cell, a natural killer cell, a B lymphocyte, a T lymphocyte, a macrophage, and a precursor cell thereof.

5. A switchable chimeric antigen receptor, comprising:

(a) the switch molecule of claim 2; and (b) a chimeric antigen receptor comprising:

i) an extracellular domain comprising an antibody, or antigen binding fragment thereof, which targets the switch molecule of claim 2;

ii) a transmembrane domain; and iii) an intracellular signaling domain.

6. The switchable chimeric antigen receptor of claim 5, wherein the transmembrane domain includes a transmembrane domain of a protein selected from the group consisting of the alpha, beta, or zeta chain of a T-cell receptor, CD27, CD28, CD3 epsilon, CD45, CD4, CD5, CD8, CD9, CD16, CD22, CD33, CD37, CD64, CD80, CD86, CD134, CD137, and CD154.

7. The switchable chimeric antigen receptor of claim 5, wherein the intracellular signaling domain includes a domain derived from a CD3ζ (CD3 zeta) chain.

8. The switchable chimeric antigen receptor of claim 5, wherein the intracellular signaling domain further comprises a costimulatory molecule selected from the group consisting of OX40 (CD134), CD2, CD27, CD28, CDS, ICAM-1, LFA-1 (CD11a/CD18), and 4-1BB (CD137).

9. The switchable chimeric antigen receptor of claim 5, wherein the antibody, or antigen binding fragment thereof, of i) is an anti-cotinine antibody.

10. The switchable chimeric antigen receptor of claim 5, wherein the antibody, or antigen binding fragment thereof, of i) comprises HCDR1 of SEQ ID NO: 9, HCDR2 of SEQ ID NO: 10, HCDR3 of SEQ ID NO: 11, LCDR1 of SEQ ID NO: 12, LCDR2 of SEQ ID NO: 13, and LCDR3 of SEQ ID NO: 14.

* * * * *